(12) United States Patent
Stoicescu

(10) Patent No.: US 12,264,142 B2
(45) Date of Patent: Apr. 1, 2025

(54) HETEROCYCLIC COMPOUNDS

(71) Applicant: FLORATEK PHARMA SA, Aubonne (CH)

(72) Inventor: Dan Florin Stoicescu, Aubonne (CH)

(73) Assignee: FLORATEK PHARMA SA, Aubonne (CH)

( * ) Notice: Subject to any disclaimer, the term of this patent is extended or adjusted under 35 U.S.C. 154(b) by 323 days.

(21) Appl. No.: 17/755,103

(22) PCT Filed: Oct. 21, 2020

(86) PCT No.: PCT/EP2020/079653
§ 371 (c)(1),
(2) Date: Apr. 21, 2022

(87) PCT Pub. No.: WO2021/078811
PCT Pub. Date: Apr. 29, 2021

(65) Prior Publication Data
US 2022/0402889 A1    Dec. 22, 2022

(30) Foreign Application Priority Data
Oct. 21, 2019  (GB) .................................... 1915191

(51) Int. Cl.
*C07D 311/80* (2006.01)
*A61P 3/00* (2006.01)
*C07D 221/06* (2006.01)
*C07D 335/04* (2006.01)

(52) U.S. Cl.
CPC .......... *C07D 311/80* (2013.01); *C07D 221/06* (2013.01); *C07D 335/04* (2013.01); *A61P 3/00* (2018.01)

(58) Field of Classification Search
CPC .. C07D 311/80; C07D 221/06; C07D 335/04; A61K 31/352; A61P 3/00
See application file for complete search history.

(56) References Cited

U.S. PATENT DOCUMENTS 5,066,671 A    11/1991  Caufield
2016/0000753 A1    1/2016  Rinsch et al.

FOREIGN PATENT DOCUMENTS

WO    WO-2015097231 A1 *    7/2015  ........... A61K 31/366

OTHER PUBLICATIONS

Cozza, et al., ChemMedChem, 2011, 6, 2273-2286.
International Search Report for PCT/EP2020/079653, dated Jan. 22, 2021.
Landete, Food Research International, 2011, 44, 1150-1160.
Pandey, et al., Bioorganic & Medicinal Chemistry, 2004, 12, 2239-2249.

* cited by examiner

*Primary Examiner* — Amanda L. Aguirre
(74) *Attorney, Agent, or Firm* — HUESCHEN AND SAGE

(57) ABSTRACT

The present invention concerns compounds of Formula (1), pharmaceutically acceptable salts, solvates or prodrugs thereof, pharmaceutical compositions comprising the same, and the use of the same in treating or preventing a disease.

Formula (I)

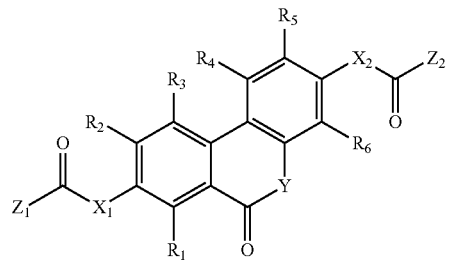

7 Claims, 6 Drawing Sheets

Day 3

Day 10

HETEROCYCLIC COMPOUNDS

BACKGROUND OF THE INVENTION

Urolithins are metabolites produced by the action of mammalian, including human, gut microbiota on ellagitannins and ellagic acid. Ellagitannins and ellagic acid are compounds commonly found in foods such as pomegranates, nuts and berries. Ellagitannins are minimally absorbed in the gut themselves. Urolithins are a class of compounds with the representative structures below and they have been shown to have potent effects on the improvement of a number of health conditions; for example see: Espin J C et al, 2013, "Biological Significance of Urolithins, the Gut Microbial Ellagic Acid-Derived Metabolites: The Evidence So Far", Evidence-Based Complementary and Alternative Medicine; Ahsan A et al, 2019, "Urolithin A-activated autophagy but not mitophagy protects against ischemic neuronal injury by inhibiting ER stress in vitro and in vivo", *CNS Neuroscience and Therapeutics*, vol. 25, pages 976-986; Andreux P A et al, 2019, "The mitophagy activator urolithin A is safe and induces a molecular signature of improved mitochondrial and cellular health in humans Nature Metabolism", vol. 1, pages 595-603; Gong Z et al, 2019, "Urolithin A attenuates memory impairment and neuroinflammation in APP/PS1 mice", *Journal of Neuroinflammation, vol.* 16; and Singh R et al, 2019, "Enhancement of the gut barrier integrity by a microbial metabolite through the Nrf2 pathway", *Nature Communications* 10:89.

In particular, the compounds Urolithin A, B, C, D, E, M5, M6, and M7 have been shown to be highly biologically active in vitro and in vivo.

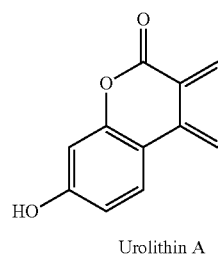

Urolithin A

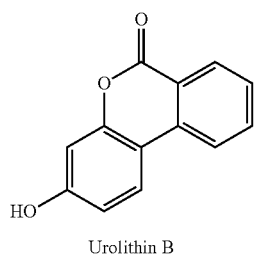

Urolithin B

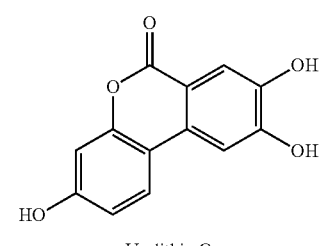

Urolithin C

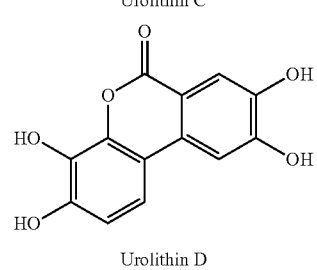

Urolithin D

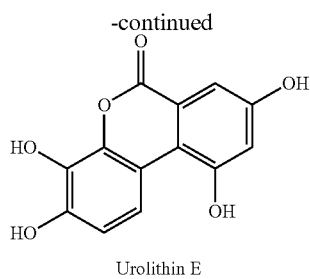

Urolithin E

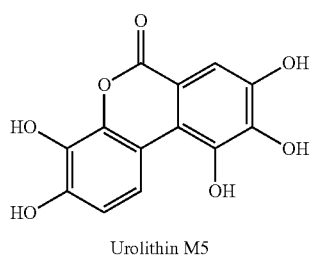

Urolithin M5

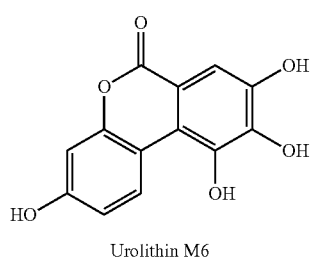

Urolithin M6

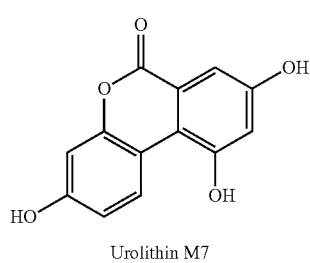

Urolithin M7

Urolithins have been proposed as treatments of a variety of conditions related to inadequate mitochondrial activity, including obesity, reduced metabolic rate, metabolic syndrome, diabetes mellitus, cardiovascular disease, hyperlipidaemia, neurodegenerative diseases, cognitive disorder, mood disorder, stress, and anxiety disorder; for weight management, or to increase muscle performance or mental performance; for example see WO2012/088519 (Amazentis SA). In WO2007/127263 (The Regents of the University of California), the use of urolithins for the treatment of various neoplastic diseases is described.

SUMMARY OF INVENTION

A first aspect of the invention provides compound of formula (I):

Formula (I)

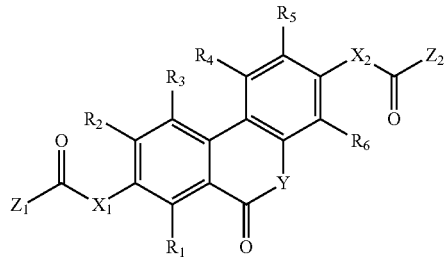

wherein:

$X_1$ and $X_2$, $Y$, independently, are selected from —O—, —S—, —NH—, —NHCH$_2$—, —NR, —CH$_2$—, and —CHR—;

R is independently selected from $C_1$-$C_6$ alkyl, $C_2$-$C_6$ alkenyl, $C_2$-$C_6$ alkynyl, —OH, and —OR$^\beta$;

$R^1$, $R^2$, $R^3$, $R^4$, $R^5$, and $R^6$, independently, are selected from H; halo; —CN; —NO$_2$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —NH$_2$; —NHR$^\beta$; —N(R$^\beta$)$_2$; —CHO; —COR$^\beta$; —COOH; —COOR$^\beta$; and —OCOR$^\beta$;

each —R$^\beta$ is independently selected from a $C_1$-$C_6$ alkyl, $C_2$-$C_6$ alkenyl, $C_2$-$C_6$ alkynyl or $C_3$-$C_{14}$ cyclic group; wherein any —R$^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH$_2$, —CN, —NO$_2$, —C≡CH, —CHO, —CON(CH$_3$)$_2$ or oxo (═O) groups;

$Z^1$ and $Z^2$, independently, are selected from —NR$^7$R$^8$ and —OR$^9$; R$^7$, R$^8$, and R$^9$, independently, are selected from H, $C_1$-$C_6$ alkyl, $C_2$-$C_6$ alkenyl, $C_2$-$C_6$ alkynyl or $C_3$-$C_{14}$ cyclic group; wherein any R$^7$, R$^8$ or R$^9$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH$_2$, —CN, —NO$_2$, —C≡CH, —CHO, —CON(CH$_3$)$_2$ or oxo (═O) groups.

In one embodiment, $X_1$ and $X_2$, independently, are selected from —O—, —S—, and —NH$_2$—.

In one embodiment, $X_1$ and $X_2$ are both —O—.

In one embodiment, Y is selected from —O—, —S—, and —NH$_2$—.

In one embodiment, Y is selected from —O— and —NH$_2$—.

In one embodiment, $R^1$, $R^2$, $R^3$, $R^4$, $R^5$, and $R^6$, independently, are selected from H; halo; —CN; —NO$_2$; —OH; —SH; —SO$_2$H; —SO$_2$NH$_2$; —NH$_2$; —CHO; and —COOH.

In one embodiment, $R^1$, $R^2$, $R^3$, $R^4$, $R^5$, and $R^6$ are H.

In one embodiment, $Z^1$ and $Z^2$, independently, are selected from —NR$^7$R$^8$.

In one embodiment, R$^7$, R$^8$, and R$^9$, independently, are selected from H, $C_1$-$C_6$ alkyl, $C_2$-$C_6$ alkenyl, and $C_2$-$C_6$ alkynyl.

In one embodiment, $Z^1$ and $Z^2$, independently, are selected from —NHR$^8$, wherein R$^8$ is as defined above. For example, R$^8$ may be selected from $C_{1-4}$ alkyl, such as methyl or ethyl.

In one embodiment, $Z^1$ and $Z^2$ are independently selected from —NHCH$_3$ and —NHCH$_2$CH$_3$.

In one embodiment, $Z^1$ and $Z^2$ are both —NHCH$_3$.

In one embodiment, $Z^1$ and $Z^2$ are both —NHCH$_2$CH$_3$.

A second aspect of the invention provides a compound of Formula (7), Formula (8), or Formula (9):

Formula (7)

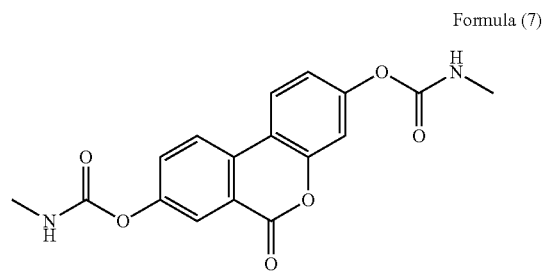

Formula (8)

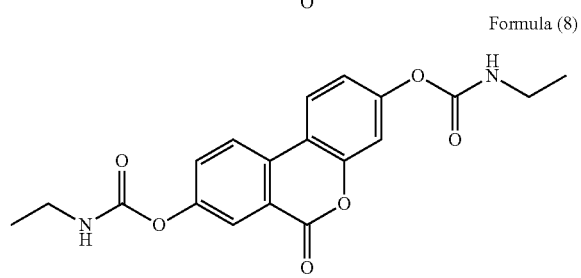

Formula (9)

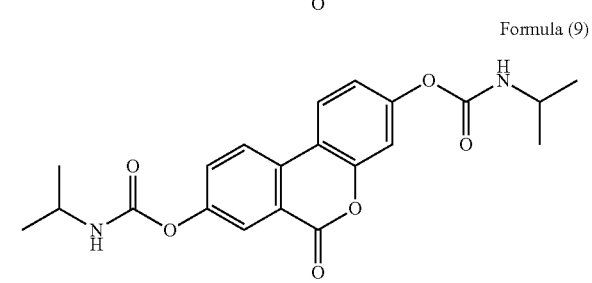

A third aspect of the invention provides pharmaceutically acceptable salt, solvate or prodrug of the compound of the first or second aspect of the invention.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

An sixth aspect of the invention provides the use of a compound of the first or second aspect, a pharmaceutically effective salt, solvate or prodrug of the third aspect, or a pharmaceutical composition according to the fourth aspect, in the manufacture of a medicament for the treatment or prevention of a disease, disorder or condition. Typically the treatment or prevention comprises the administration of the compound, salt, solvate, prodrug or pharmaceutical composition to a subject. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. Typically the administration is to a subject in need thereof. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

DEFINITIONS

Figure 1:
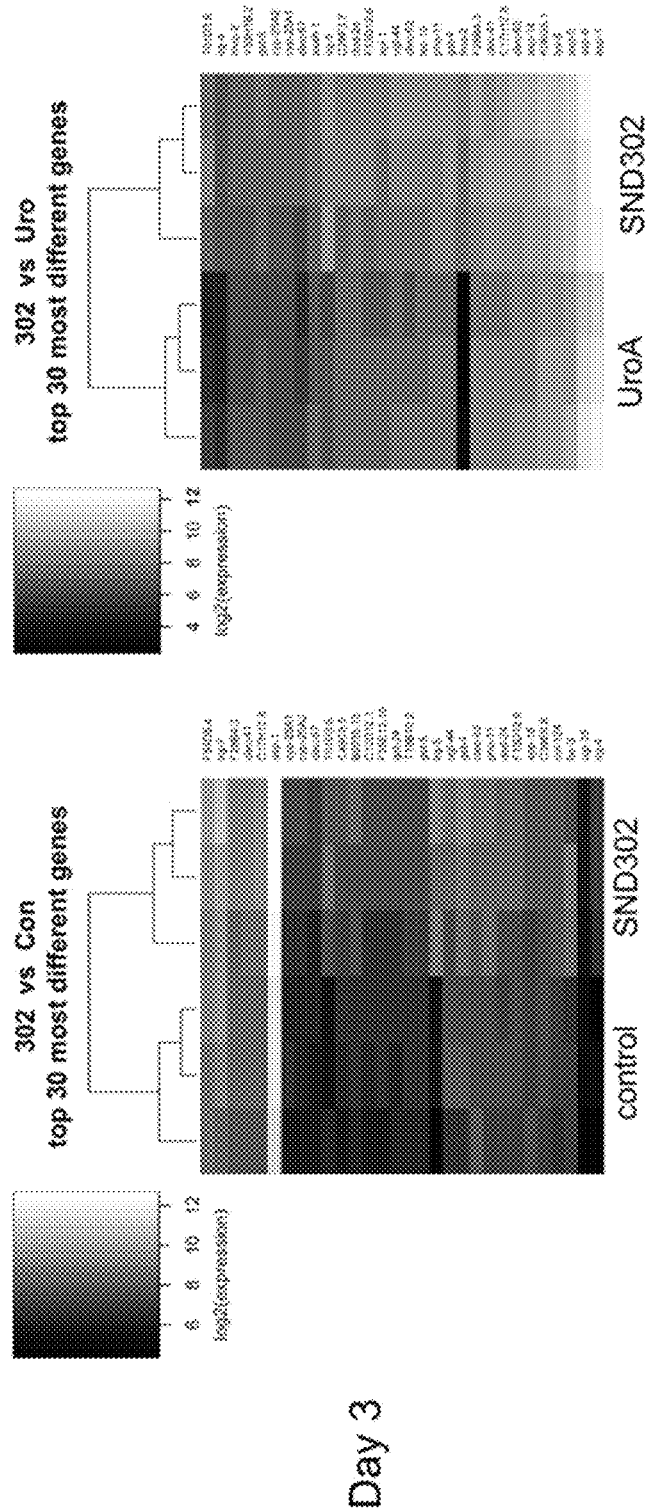
FIG. 1 shows heat maps and table depicting top 30 differentially-expressed genes in SND302-treated vs. control (Uro-A or Vehicle) animals at day 3 of adulthood. Black indicates downregulated genes and white upregulated genes.

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_{12}$ hydrocarbyl group. More typically a hydrocarbyl group is a $C_1$-$C_{10}$ hydrocarbyl group. A "hydrocarbylene" group is similarly defined as a divalent hydrocarbyl group.

An "alkyl" substituent group or an alkyl moiety in a substituent group may be linear or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "haloalkyl" substituent group or haloalkyl group in a substituent group refers to an alkyl, alkenyl, or alkynyl substituent group or moiety including one or more carbon atoms and one or more halo atoms, e.g. Cl, Br, I, or F. Each halo atom replaces a hydrogen of the alkyl, alkenyl, or alkynyl substituent group or moiety. Examples include —CH$_2$F—CHF$_2$, —CHI$_2$, —CHBr$_2$, —CHCl$_2$, —CF$_3$, —CH$_2$CF$_3$ and CF$_2$CH$_3$. Suitable haloalkyls include but are not limited to —CF$_3$, and —CH$_2$CF$_3$.

An "alkoxy" substituent group or alkoxy group in a substituent group refers to an alkyl, alkenyl, or alkynyl substituent group or moiety including one or more carbon atoms and one or more oxygen atoms. Each oxygen atom replaces a carbon atom (for example the terminal or bonding carbon) of the alkyl, alkenyl, or alkynyl substituent group or moiety. Examples include —OCH$_3$, —OCH$_2$CH$_3$, —OCH$_2$CH$_2$CH$_3$, and —OCH(CH$_3$)(CH$_3$).

An "alkylthio" substituent group or alkylthio group in a substituent group refers to an alkyl, alkenyl, or alkynyl substituent group or moiety including one or more carbon atoms and one or more sulphur atoms. Each sulphur atom replaces a carbon atom (for example the terminal or bonding carbon) of the alkyl, alkenyl, or alkynyl substituent group or moiety. Examples include —SCH$_3$, —SCH$_2$CH$_3$, —SCH$_2$CH$_2$CH$_3$, and —SCH(CH$_3$)(CH$_3$).

An "alkylsulfinyl" substituent group or alkylsulfinyl group in a substituent group refers to an alkyl, alkenyl, or alkynyl substituent group or moiety including one or more carbon atoms and one or more sulfinyl groups (—S(=O)—). Each sulfinyl group replaces a carbon atom (for example the terminal or bonding carbon) of the alkyl, alkenyl, or alkynyl substituent group or moiety. Examples include —S(=O)CH$_3$, —S(=O)CH$_2$CH$_3$, —S(=O)CH$_2$CH$_2$CH$_3$, and —S(=O)CH(CH$_3$)(CH$_3$).

An "alkylsulfonyl" substituent group or alkylsulfonyl group in a substituent group refers to an alkyl, alkenyl, or alkynyl substituent group or moiety including one or more carbon atoms and one or more sulfonyl groups (—SO$_2$—). Each sulfonyl group replaces a carbon atom (for example the terminal or bonding carbon) of the alkyl, alkenyl, or alkynyl substituent group or moiety. Examples include —SO$_2$(CH$_3$), —SO$_2$(CH$_2$CH$_3$), —SO$_2$(CH$_2$CH$_2$CH$_3$), and —SO$_2$(CH(CH$_3$)(CH$_3$)).

An "arylsulfonyl" substituent group or arylsulfonyl group in a substituent group refers to an aryl substituent group or moiety including one or more carbon atoms and one or more sulfonyl groups (—SO$_2$—). Each sulfonyl group replaces a carbon atom (for example the terminal or bonding carbon) of the alkyl, alkenyl, or alkynyl substituent group or moiety. Examples include —SO$_2$(CH$_3$), —SO$_2$(CH$_2$CH$_3$), —SO$_2$(CH$_2$CH$_2$CH$_3$), and —SO$_2$(CH(CH$_3$)(CH$_3$)).

A "cyclic" substituent group or a cyclic moiety in a substituent group refers to any hydrocarbyl ring, wherein the hydrocarbyl ring may be saturated or unsaturated and may include one or more heteroatoms, e.g. N, O or S, in its carbon skeleton. Examples of cyclic groups include aliphatic cyclic, cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

A "heterocyclic" substituent group or a heterocyclic moiety in a substituent group refers to a cyclic group or moiety including one or more carbon atoms and one or more heteroatoms, e.g. N, O or S, in the ring structure. Examples of heterocyclic groups include heteroaryl groups as discussed below and non-aromatic heterocyclic groups such as azetidinyl, azetinyl, tetrahydrofuranyl, pyrrolidinyl, tetrahydrothiophenyl, tetrahydropyranyl, piperidinyl, piperazinyl, morpholinyl and thiomorpholinyl groups.

An "aliphatic cyclic" substituent group or aliphatic cyclic moiety in a substituent group refers to a hydrocarbyl cyclic group or moiety that is not aromatic. The aliphatic cyclic group may be saturated or unsaturated and may include one or more heteroatoms, e.g. N, O or S, in its carbon skeleton. Examples include cyclopropyl, cyclohexyl and morpholinyl. Unless stated otherwise, an aliphatic cyclic substituent group or moiety may include monocyclic, bicyclic or polycyclic hydrocarbyl rings.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding any ring systems which are part of or formed by optional substituents) are aromatic. Examples of heteroaryl groups/moieties include the following:

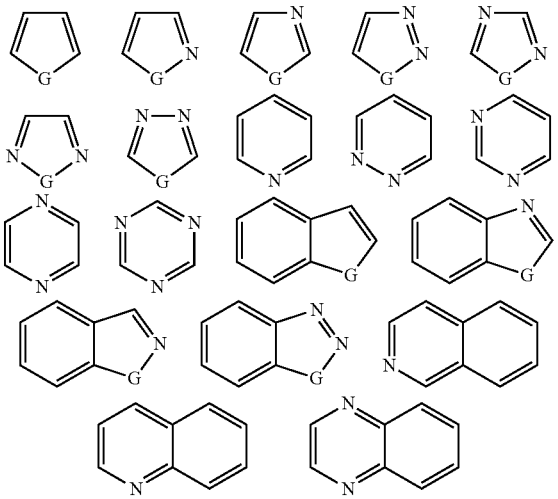

wherein G=O, S or NH.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

Typically a substituted group comprises 1, 2, 3 or 4 substituents, more typically 1, 2 or 3 substituents, more typically 1 or 2 substituents, and even more typically 1 substituent.

Unless stated otherwise, any divalent bridging substituent (e.g. —O—, —S—, —NH—, —N(R$^\beta$)— or —R$^\alpha$—) of an optionally substituted group or moiety must only be attached to the specified group or moiety and may not be attached to a second group or moiety, even if the second group or moiety can itself be optionally substituted.

The term "halo" includes fluoro, chloro, bromo and iodo.

Where reference is made to a carbon atom of a group being replaced by an N, O or S atom, what is intended is that:

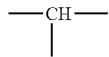

is replaced by

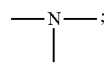

—$CH_2$— is replaced by —NH—, —O— or —S—;
—$CH_3$ is replaced by —$NH_2$, —OH, or —SH;
—CH= is replaced by —N=;
$CH_2$= is replaced by NH=, O= or S=; or
CH≡ is replaced by N≡.

In the context of the present specification, unless otherwise stated, a $C_x$-$C_y$ group is defined as a group containing from x to y carbon atoms. For example, a $C_1$-$C_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are counted as carbon atoms when calculating the number of carbon atoms in a $C_x$-$C_y$ group. For example, a morpholinyl group is to be considered a $C_6$ heterocyclic group, not a $C_4$ heterocyclic group.

A "protecting group" refers to a grouping of atoms that when attached to a reactive functional group (e.g. OH) in a compound masks, reduces or prevents reactivity of the functional group.

In the context of the present specification, = is a double bond; ≡ is a triple bond.

DETAILED DESCRIPTION

A first aspect of the invention provides a compound of formula (I):

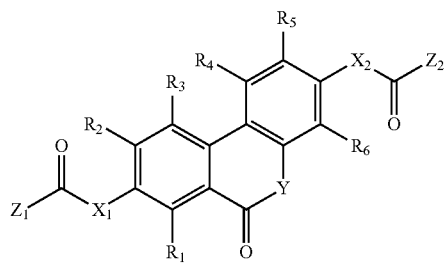

Formula (I)

wherein:
Y, $X_1$ and $X_2$, independently, are selected from —O—, —S—, —NH—, —$NHCH_2$—, —NR, —$CH_2$—, and —CHR—;

R is independently selected from $C_1$-$C_6$ alkyl, $C_2$-$C_6$ alkenyl, $C_2$-$C_6$ alkynyl, —OH, and —$OR^β$;

$R^1$, $R^2$, $R^3$, $R^4$, $R^5$, and $R^6$, independently, are selected from H; halo; —CN; —$NO_2$; —$R^β$; —OH; —$OR^β$; —SH; —$SR^β$; —$SOR^β$; —$SO_2H$; —$SO_2R^β$; —$SO_2NH_2$; —$SO_2NHR^β$; —$SO_2N(R^β)_2$; —$NH_2$; —$NHR^β$; —$N(R^β)_2$; —CHO; —$COR^β$; —COOH; —$COOR^β$; and —$OCOR^β$;

each —$R^β$ is independently selected from a $C_1$-$C_6$ alkyl, $C_2$-$C_6$ alkenyl, $C_2$-$C_6$ alkynyl or $C_3$-$C_{14}$ cyclic group; wherein any —$R^β$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups;

$Z^1$ and $Z^2$, independently, are selected from —$NR^7R^8$ and —$OR^9$;

$R^7$, $R^8$, and $R^9$, independently, are selected from H, $C_1$-$C_6$ alkyl, $C_2$-$C_6$ alkenyl, $C_2$-$C_6$ alkynyl or $C_3$-$C_{14}$ cyclic group; wherein any $R^7$, $R^8$ or $R^9$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups.

In one embodiment, the compounds of formula (I) are not wherein Y is O, $X^1$ and $X^2$ are O, $R^1$-$R^6$ are H, and:
(i) $Z^1$ and $Z^2$ are —$N(CH_3)_2$; or
(ii) $Z^1$ and $Z^2$ are —$N(C_2H_5)_2$.

In one embodiment, $X_1$ and $X_2$, independently, are selected from —O—, —S—, and —NH—.

In one embodiment, $X_1$ and $X_2$ are —O—.

In one embodiment, $X_1$ and $X_2$ are —NH—.

In one embodiment, Y is selected from —O—, —S—, and —NH—.

In one embodiment, Y is —O—.

In one embodiment, Y is —NH—.

In one embodiment, Y, $X_1$ and $X_2$, independently, are selected from —O—, —S—, —NH—.

In one embodiment, Y, $X_1$ and $X_2$ are all —O—.

In one embodiment, R is a $C_1$-$C_6$ alkyl, such as a $C_1$-$C_4$ alkyl.

In one embodiment, R is methyl.

In one embodiment, $R^1$, $R^2$, $R^3$, $R^4$, $R^5$, and $R^6$, independently, are selected from H; halo; —CN; —$NO_2$; —OH; —SH; —$SO_2H$; —$SO_2NH_2$; —$NH_2$; —CHO; and —COOH.

In one embodiment, $R^1$, $R^2$, $R^3$, $R^4$, $R^5$, and $R^6$ are H.

In one embodiment, $Z^1$ and $Z^2$, independently, are selected from —$NR^7R^8$.

In one embodiment, $R^7$, $R^8$, and $R^9$, independently, are selected from H, $C_1$-$C_6$ alkyl, $C_2$-$C_6$ alkenyl, and $C_2$-$C_6$ alkynyl.

In one embodiment, $Z^1$ and $Z^2$, independently, are selected from —$NHR^8$, wherein $R^8$ is as defined above. For example, $R^8$ may be selected from $C_{1-4}$ alkyl, such as methyl or ethyl. Alternatively, $R^8$ may be propyl, such as i-propyl.

In one embodiment, $Z^1$ and $Z^2$ are independently selected from —$NHCH_3$ and —$NHCH_2CH_3$.

In one embodiment, $Z^1$ and $Z^2$ are both —$NHCH_3$.

In one embodiment, $Z^1$ and $Z^2$ are both —$NHCH_2CH_3$.

In one embodiment, $Z^1$ and $Z^2$ are both —$NHCH(CH_3)_2$.

In one embodiment, $X^1$ and $X^2$ are O; and $Z^1$ and $Z^2$ are —$NHR^8$. For example, $R^8$ may be $C_{1-4}$ alkyl.

In one embodiment, Y, $X_1$ and $X_2$, independently, are selected from —O—, —S—, and —NH—; $R^1$, $R^2$, $R^3$, $R^4$, $R^5$, and $R^6$, independently, are selected from H; halo; —CN;

—NO₂; —OH; —SH; —SO₂H; —SO₂NH₂; —NH₂; —CHO; and —COOH; $Z^1$ and $Z^2$, independently, are selected from —NR⁷R⁸; and R⁷, R⁸, and R⁹, independently, are selected from H, $C_1$-$C_6$ alkyl, $C_2$-$C_6$ alkenyl, and $C_2$-$C_6$ alkynyl. In one embodiment, $Z^1$ and $Z^2$ are both —NHCH₃. In one embodiment, $Z^1$ and $Z^2$ are both —NHCH₂CH₃.

In one embodiment, the compound of formula (i) is a compound of formula (2):

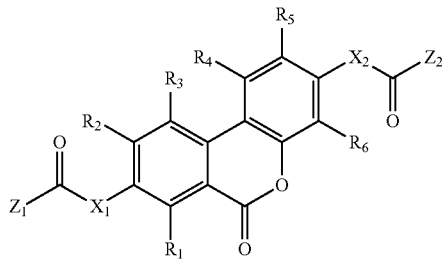

Formula (2)

wherein:

$Z^1$ and $Z^2$, independently, are selected from —NR⁷R⁸ and —OR⁹, $X_1$ and $X_2$, independently, are selected from —O—, —S—, —NH—, —NHCH₂—, —NR, —CH₂—, and —CHR—;

R is independently selected from $C_1$-$C_6$ alkyl, $C_2$-$C_6$ alkenyl, $C_2$-$C_6$ alkynyl, —OH, and —OR^β;

R¹, R², R³, R⁴, R⁵, and R⁶, independently, are selected from H; halo; —CN; —NO₂; —R^β; —OH; —OR^β; —SH; —SR^β; —SOR^β; —SO₂H; —SO₂R^β; —SO₂NH₂; —SO₂NHR^β; —SO₂N(R^β)₂; —NH₂; —NHR^β; —N(R^β)₂; —CHO; —COR^β; —COOH; —COOR^β; and —OCOR^β; each —R^β is independently selected from a $C_1$-$C_6$ alkyl, $C_2$-$C_6$ alkenyl, $C_2$-$C_6$ alkynyl or $C_3$-$C_{14}$ cyclic group; wherein any —R^β may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH₂, —CN, —NO₂, —C≡CH, —CHO, —CON(CH₃)₂ or oxo (═O) groups;

R⁷, R⁸, and R⁹, independently, are selected from H, $C_1$-$C_6$ alkyl, $C_2$-$C_6$ alkenyl, $C_2$-$C_6$ alkynyl or $C_3$-$C_{14}$ cyclic group; wherein any R⁷, R⁸ or R⁹ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH₂, —CN, —NO₂, —C≡CH, —CHO, —CON(CH₃)₂ or oxo (═O) groups.

In one embodiment, the compound is a compound of formula (2) in which $X_1$ and $X_2$, independently, are selected from —O—, —S—, and —NH—. For example, $X_1$ and $X_2$ may both be —O—.

In one embodiment, the compound is a compound of formula (2) in which R¹, R², R³, R⁴, R⁵, and R⁶, independently, are selected from H; halo; —CN; —NO₂; —OH; —SH; —SO₂H; —SO₂NH₂; —NH₂; —CHO; and —COOH. For example, in one embodiment, R¹, R², R³, R⁴, R⁵, and R⁶ are H.

In one embodiment, $X^1$ and $X^2$ are both —O—.

In one embodiment, $Z^1$ and $Z^2$ are independently selected from —NHCH₃ and —NHCH₂CH₃.

In one embodiment, $Z^1$ and $Z^2$ are both —NHCH₃.

In one embodiment, $Z^1$ and $Z^2$ are both —NHCH₂CH₃.

In one embodiment, $Z^1$ and $Z^2$ are both —NHCH(CH₃)₂.

In one embodiment, $X^1$ and $X^2$ are O; and $Z^1$ and $Z^2$ are —NHR⁸. For example, R⁸ may be $C_{1-4}$ alkyl.

In one embodiment, the compound is a compound of formula (2) in which $Z^1$ and $Z^2$, independently, are selected from —NR⁷R⁸. For example, in one embodiment, R⁷, R⁸, and R⁹, independently, are selected from H, $C_1$-$C_6$ alkyl, $C_2$-$C_6$ alkenyl, and $C_2$-$C_6$ alkynyl. For example, in one embodiment, $Z^1$ and $Z^2$, independently, are selected from —NHR⁸, wherein R⁸ is as defined above. For example, R⁸ may be selected from $C_{1-4}$ alkyl, such as methyl or ethyl. In one embodiment, $Z^1$ and $Z^2$ are both —NHCH₃. In one embodiment, $Z^1$ and $Z^2$ are both —NHCH₂CH₃.

In one embodiment, the compound is a compound of formula (2) in which R¹, R², R³, R⁴, R⁵, and R⁶, independently, are selected from H; halo; —CN; —NO₂; —OH; —SH; —SO₂H; —SO₂NH₂; —NH₂; —CHO; and —COOH; $X_1$ and $X_2$, independently, are selected from —O—, —S—, and —NH—; $Z^1$ and $Z^2$, independently, are selected from —NR⁷R⁸; and R⁷, R⁸, and R⁹, independently, are selected from H, $C_1$-$C_6$ alkyl, $C_2$-$C_6$ alkenyl, and $C_2$-$C_6$ alkynyl. In one embodiment, $Z^1$ and $Z^2$ are both —NHCH₃. In one embodiment, $Z^1$ and $Z^2$ are both —NHCH₂CH₃.

In one embodiment, the compound is a compound of formula (2) in which R¹, R², R³, R⁴, R⁵, and R⁶, independently, are H; $X_1$ and $X_2$ are selected —O—; $Z^1$ and $Z^2$, independently, are selected from —NR⁷R⁸; and R⁷, R⁸, and R⁹, independently, are selected from H, and $C_1$-$C_4$ alkyl. In one embodiment, $Z^1$ and $Z^2$ are both —NHCH₃. In one embodiment, $Z^1$ and $Z^2$ are both —NHCH₂CH₃.

In one embodiment, the compound is a compound of formula (3):

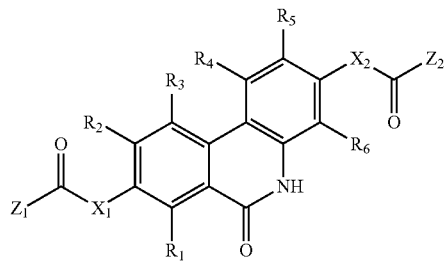

Formula (3)

wherein:

$Z^1$ and $Z^2$, independently, are selected from —NR⁷R⁸ and —OR⁹, $X_1$ and $X_2$, independently, are selected from —O—, —S—, —NH—, —NHCH₂—, —NR, —CH₂—, and —CHR—;

R is independently selected from $C_1$-$C_6$ alkyl, $C_2$-$C_6$ alkenyl, $C_2$-$C_6$ alkynyl, —OH, and —OR^β;

R¹, R², R³, R⁴, R⁵, and R⁶, independently, are selected from H; halo; —CN; —NO₂; —R^β; —OH; —OR^β; —SH; —SR^β; —SOR^β; —SO₂H; —SO₂R^β; —SO₂NH₂; —SO₂NHR^β; —SO₂N(R^β)₂; —NH₂; —NHR^β; —N(R^β)₂; —CHO; —COR^β; —COOH; —COOR^β; and —OCOR^β; each —R^β is independently selected from a $C_1$-$C_6$ alkyl, $C_2$-$C_6$ alkenyl, $C_2$-$C_6$ alkynyl or $C_3$-$C_{14}$ cyclic group; wherein any —R^β may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH$_2$, —CN, —NO$_2$, —C≡CH, —CHO, —CON(CH$_3$)$_2$ or oxo (=O) groups;

R$^7$, R$^8$, and R$^9$, independently, are selected from H, C$_1$-C$_6$ alkyl, C$_2$-C$_6$ alkenyl, C$_2$-C$_6$ alkynyl or C$_3$-C$_{14}$ cyclic group; wherein any R$^7$, R$^8$ or R$^9$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —NO$_2$, —C≡CH, —CHO, —CON(CH$_3$)$_2$ or oxo (=O) groups.

In one embodiment, the compound is a compound of formula (3) in which Z$^1$ and Z$^2$, independently, are selected from —NR$^7$R$^8$. For example, in one embodiment, R$^7$, R$^8$, and R$^9$, independently, are selected from H, C$_1$-C$_6$ alkyl, C$_2$-C$_6$ alkenyl, and C$_2$-C$_6$ alkynyl. For example, in one embodiment, Z$^1$ and Z$^2$, independently, are selected from —NHR$^8$, wherein R$^8$ is as defined above. For example, R$^8$ may be selected from C$_{1-4}$ alkyl, such as methyl or ethyl. In one embodiment, Z$^1$ and Z$^2$ are both —NHCH$_3$.

In one embodiment, the compound is a compound of formula (3) in which X$_1$ and X$_2$, independently, are selected from —O—, —S—, and —NH—. For example, X$_1$ and X$_2$ may both be —O—.

In one embodiment, the compound is a compound of formula (3) in which R$^1$, R$^2$, R$^3$, R$^4$, R$^5$, and R$^6$, independently, are selected from H; halo; —CN; —NO$_2$; —OH; —SH; —SO$_2$H; —SO$_2$NH$_2$; —NH$_2$; —CHO; and —COOH. For example, in one embodiment, R$^1$, R$^2$, R$^3$, R$^4$, R$^5$, and R$^6$ are H.

In one embodiment, the compound is a compound of formula (3) in which R$^1$, R$^2$, R$^3$, R$^4$, R$^5$, and R$^6$, independently, are selected from H; halo; —CN; —NO$_2$; —OH; —SH; —SO$_2$H; —SO$_2$NH$_2$; —NH$_2$; —CHO; and —COOH; X$_1$ and X$_2$, independently, are selected from —O—, —S—, and —NH—; Z$^1$ and Z$^2$, independently, are selected from —NR$^7$R$^8$; and R$^7$, R$^8$, and R$^9$, independently, are selected from H, C$_1$-C$_6$ alkyl, C$_2$-C$_6$ alkenyl, and C$_2$-C$_6$ alkynyl.

In one embodiment, the compound is a compound of formula (3) in which R$^1$, R$^2$, R$^3$, R$^4$, R$^5$, and R$^6$, independently, are H; X$_1$ and X$_2$ are —O—; Z$^1$ and Z$^2$, independently, are selected from —NR$^7$R$^8$; and R$^7$, R$^8$, and R$^9$, independently, are selected from H, and C$_1$-C$_4$ alkyl.

In one embodiment, Z$^1$ and Z$^2$ are independently selected from —NHCH$_3$ and —NHCH$_2$CH$_3$.

In one embodiment, Z$^1$ and Z$^2$ are both —NHCH$_3$.
In one embodiment, Z$^1$ and Z$^2$ are both —NHCH$_2$CH$_3$.
In one embodiment, Z$^1$ and Z$^2$ are both —NHCH(CH$_3$)$_2$.
In one embodiment, X$^1$ and X$^2$ are O; and Z$^1$ and Z$^2$ are —NHR$^8$. For example, R$^8$ may be C$_{1-4}$ alkyl.

In one embodiment, the compound is a compound of formula (4):

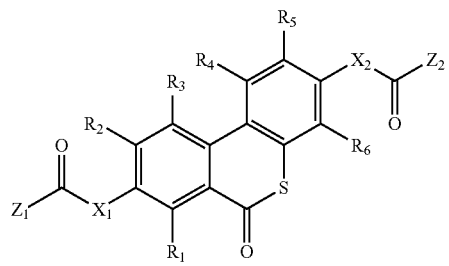

Formula (4)

wherein:

Z$^1$ and Z$^2$, independently, are selected from —NR$^7$R$^8$ and —OR$^9$,

X$_1$ and X$_2$, independently, are selected from —O—, —S—, —NH—, —NHCH$_2$—, —NR, —CH$_2$—, and —CHR—;

R is independently selected from C$_1$-C$_6$ alkyl, C$_2$-C$_6$ alkenyl, C$_2$-C$_6$ alkynyl, —OH, and —OR$^\beta$;

R$^1$, R$^2$, R$^3$, R$^4$, R$^5$, and R$^6$, independently, are selected from H; halo; —CN; —NO$_2$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —NH$_2$; —NHR$^\beta$; —N(R$^\beta$)$_2$; —CHO; —COR$^\beta$; —COOH; —COOR$^\beta$; and —OCOR$^\beta$; each —R$^\beta$ is independently selected from a C$_1$-C$_6$ alkyl, C$_2$-C$_6$ alkenyl, C$_2$-C$_6$ alkynyl or C$_3$-C$_{14}$ cyclic group; wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —NO$_2$, —C≡CH, —CHO, —CON(CH$_3$)$_2$ or oxo (=O) groups;

R$^7$, R$^8$, and R$^9$, independently, are selected from H, C$_1$-C$_6$ alkyl, C$_2$-C$_6$ alkenyl, C$_2$-C$_6$ alkynyl or C$_3$-C$_{14}$ cyclic group; wherein any R$^7$, R$^8$ or R$^9$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —NO$_2$, —C≡CH, —CHO, —CON(CH$_3$)$_2$ or oxo (=O) groups.

In one embodiment, the compound is a compound of formula (4) in which Z$^1$ and Z$^2$, independently, are selected from —NR$^7$R$^8$. For example, in one embodiment, R$^7$, R$^8$, and R$^9$, independently, are selected from H, C$_1$-C$_6$ alkyl, C$_2$-C$_6$ alkenyl, and C$_2$-C$_6$ alkynyl. For example, in one embodiment, Z$^1$ and Z$^2$, independently, are selected from —NHR$^8$, wherein R$^8$ is as defined above. For example, R$^8$ may be selected from C$_{1-4}$ alkyl, such as methyl or ethyl. In one embodiment, Z$^1$ and Z$^2$ are both —NHCH$_3$.

In one embodiment, the compound is a compound of formula (4) in which X$_1$ and X$_2$, independently, are selected from —O—, —S—, and —NH—. For example, X$_1$ and X$_2$ may both be —O—.

In one embodiment, the compound is a compound of formula (4) in which R$^1$, R$^2$, R$^3$, R$^4$, R$^5$, and R$^6$, independently, are selected from H; halo; —CN; —NO$_2$; —OH; —SH; —SO$_2$H; —SO$_2$NH$_2$; —NH$_2$; —CHO; and —COOH. For example, in one embodiment, R$^1$, R$^2$, R$^3$, R$^4$, R$^5$, and R$^6$ are H.

In one embodiment, the compound is a compound of formula (4) in which R$^1$, R$^2$, R$^3$, R$^4$, R$^5$, and R$^6$, independently, are selected from H; halo; —CN; —NO$_2$; —OH; —SH; —SO$_2$H; —SO$_2$NH$_2$; —NH$_2$; —CHO; and —COOH; X$_1$ and X$_2$, independently, are selected from —O—, —S—, and —NH—; Z$^1$ and Z$^2$, independently, are selected from —NR$^7$R$^8$; and R$^7$, R$^8$, and R$^9$, independently, are selected from H, C$_1$-C$_6$ alkyl, C$_2$-C$_6$ alkenyl, and C$_2$-C$_6$ alkynyl.

In one embodiment, the compound is a compound of formula (4) in which R$^1$, R$^2$, R$^3$, R$^4$, R$^5$, and R$^6$, independently, are H; X$_1$ and X$_2$ are —O—; Z$^1$ and Z$^2$, independently, are selected from —NR$^7$R$^8$; and R$^7$, R$^8$, and R$^9$, independently, are selected from H, and C$_1$-C$_4$ alkyl.

In one embodiment, Z$^1$ and Z$^2$ are independently selected from —NHCH$_3$ and —NHCH$_2$CH$_3$.

In one embodiment, Z$^1$ and Z$^2$ are both —NHCH$_3$.
In one embodiment, Z$^1$ and Z$^2$ are both —NHCH$_2$CH$_3$.
In one embodiment, Z$^1$ and Z$^2$ are both —NHCH(CH$_3$)$_2$.

In one embodiment, $X^1$ and $X^2$ are O; and $Z^1$ and $Z^2$ are —$NHR^8$. For example, $R^8$ may be $C_{1-4}$ alkyl.

In one embodiment, the compound is a compound of formula (5):

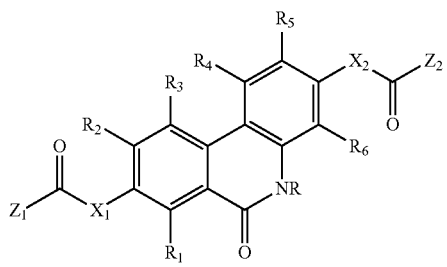

Formula (5)

wherein:
$Z^1$ and $Z^2$, independently, are selected from —$NR^7R^8$ and —$OR^9$;

$X_1$ and $X_2$, independently, are selected from —O—, —S—, —NH—, —$NHCH_2$—, —NR, —$CH_2$—, and —CHR—;

R is independently selected from $C_1$-$C_6$ alkyl, $C_2$-$C_6$ alkenyl, $C_2$-$C_6$ alkynyl, —OH, and —$OR^\beta$;

$R^1$, $R^2$, $R^3$, $R^4$, $R^5$, and $R^6$, independently, are selected from H; halo; —CN; —$NO_2$; —$R^\beta$; —OH; —$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$NH_2$; —$NHR^\beta$; —$N(R^\beta)_2$; —CHO; —$COR^\beta$; —COOH; —$COOR^\beta$; and —$OCOR^\beta$; each —$R^\beta$ is independently selected from a $C_1$-$C_6$ alkyl, $C_2$-$C_6$ alkenyl, $C_2$-$C_6$ alkynyl or $C_3$-$C_{14}$ cyclic group; wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —$CON(CH_3)_2$ or oxo (=O) groups;

$R^7$, $R^8$, and $R^9$, independently, are selected from H, $C_1$-$C_6$ alkyl, $C_2$-$C_6$ alkenyl, $C_2$-$C_6$ alkynyl or $C_3$-$C_{14}$ cyclic group; wherein any $R^7$, $R^8$ or $R^9$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —CON($CH_3$)$_2$ or oxo (=O) groups.

In one embodiment, the compound is a compound of formula (5) in which $Z^1$ and $Z^2$, independently, are selected from —$NR^7R^8$. For example, in one embodiment, $R^7$, $R^8$, and $R^9$, independently, are selected from H, $C_1$-$C_6$ alkyl, $C_2$-$C_6$ alkenyl, and $C_2$-$C_6$ alkynyl. For example, in one embodiment, $Z^1$ and $Z^2$, independently, are selected from —$NHR^8$, wherein $R^8$ is as defined above. For example, $R^8$ may be selected from $C_{1-4}$ alkyl, such as methyl or ethyl. In one embodiment, $Z^1$ and $Z^2$ are both —$NHCH_3$.

In one embodiment, the compound is a compound of formula (5) in which R is $C_1$-$C_6$ alkyl. For example, R may be $C_1$-$C_4$ alkyl. For example, R may be methyl.

In one embodiment, the compound is a compound of formula (5) in which $X_1$ and $X_2$, independently, are selected from —O—, —S—, and —NH—. For example, $X_1$ and $X_2$ may both be —O—.

In one embodiment, $Z^1$ and $Z^2$ are independently selected from —$NHCH_3$ and —$NHCH_2CH_3$.

In one embodiment, $Z^1$ and $Z^2$ are both —$NHCH_3$.

In one embodiment, $Z^1$ and $Z^2$ are both —$NHCH_2CH_3$.

In one embodiment, $Z^1$ and $Z^2$ are both —$NHCH(CH_3)_2$.

In one embodiment, $X^1$ and $X^2$ are O; and $Z^1$ and $Z^2$ are —$NHR^8$. For example, $R^8$ may be $C_{1-4}$ alkyl.

In one embodiment, the compound is a compound of formula (5) in which $R^1$, $R^2$, $R^3$, $R^4$, $R^5$, and $R^6$, independently, are selected from H; halo; —CN; —$NO_2$; —OH; —SH; —$SO_2H$; —$SO_2NH_2$; —$NH_2$; —CHO; and —COOH. For example, in one embodiment, $R^1$, $R^2$, $R^3$, $R^4$, $R^5$, and $R^6$ are H.

In one embodiment, the compound is a compound of formula (5) in which R is $C_1$-$C_4$ alkyl; $R^1$, $R^2$, $R^3$, $R^4$, $R^5$, and $R^6$, independently, are selected from H; halo; —CN; —$NO_2$; —OH; —SH; —$SO_2H$; —$SO_2NH_2$; —$NH_2$; —CHO; and —COOH; $X_1$ and $X_2$, independently, are selected from —O—, —S—, and —NH—; $Z^1$ and $Z^2$, independently, are selected from —$NR^7R^8$; and $R^7$, $R^8$, and $R^9$, independently, are selected from H, $C_1$-$C_6$ alkyl, $C_2$-$C_6$ alkenyl, and $C_2$-$C_6$ alkynyl.

In one embodiment, the compound is a compound of formula (5) in which R is $C_1$-$C_4$ alkyl; $R^1$, $R^2$, $R^3$, $R^4$, $R^5$, and $R^6$, independently, are H; $X_1$ and $X_2$ are —O—; $Z^1$ and $Z^2$, independently, are selected from —$NR^7R^8$; and $R^7$, $R^8$, and $R^9$, independently, are selected from H, and $C_1$-$C_4$ alkyl.

In one embodiment, the compound of formula (1) is a compound of formula (6):

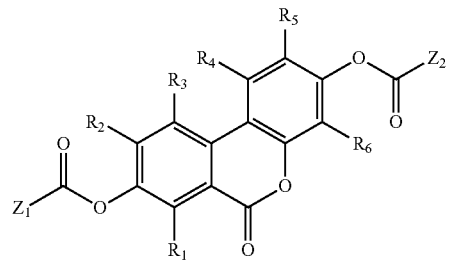

wherein:
$Z^1$ and $Z^2$, independently, are selected from —$NR^7R^8$ and —$OR^9$, $R^1$, $R^2$, $R^3$, $R^4$, $R^5$, and $R^6$, independently, are selected from H; halo; —CN; —$NO_2$; —$R^\beta$; —OH; —$OR^\beta$; —SH; —$SR^\beta$; —$SOR^\beta$; —$SO_2H$; —$SO_2R^\beta$; —$SO_2NH_2$; —$SO_2NHR^\beta$; —$SO_2N(R^\beta)_2$; —$NH_2$; —$NHR^\beta$; —$N(R^\beta)_2$; —CHO; —$COR^\beta$; —COOH; —$COOR^\beta$; and —$OCOR^\beta$; each —$R^\beta$ is independently selected from a $C_1$-$C_6$ alkyl, $C_2$-$C_6$ alkenyl, $C_2$-$C_6$ alkynyl or $C_3$-$C_{14}$ cyclic group; wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —CON($CH_3$)$_2$ or oxo (=O) groups;

$R^7$, $R^8$, and $R^9$, independently, are selected from H, $C_1$-$C_6$ alkyl, $C_2$-$C_6$ alkenyl, $C_2$-$C_6$ alkynyl or $C_3$-$C_{14}$ cyclic group; wherein any $R^7$, $R^8$ or $R^9$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —$NO_2$, —C≡CH, —CHO, —CON($CH_3$)$_2$ or oxo (=O) groups.

In one embodiment, the compound is a compound of formula (6) in which $R^1$, $R^2$, $R^3$, $R^4$, $R^5$, and $R^6$, independently, are selected from H; halo; —CN; —$NO_2$; —OH;

—SH; —SO$_2$H; —SO$_2$NH$_2$; —NH$_2$; —CHO; and —COOH. For example, in one embodiment, R$^1$, R$^2$, R$^3$, R$^4$, R$^5$, and R$^6$ are H.

In one embodiment, Z$^1$ and Z$^2$ are independently selected from —NHCH$_3$ and —NHCH$_2$CH$_3$.

In one embodiment, Z$^1$ and Z$^2$ are both —NHCH$_3$.

In one embodiment, Z$^1$ and Z$^2$ are both —NHCH$_2$CH$_3$.

In one embodiment, Z$^1$ and Z$^2$ are both —NHCH(CH$_3$)$_2$.

In one embodiment, Z$^1$ and Z$^2$ are —NHR$^8$. For example, R$^8$ may be C$_{1-4}$ alkyl.

In one embodiment, the compound is a compound of formula (6) in which Z$^1$ and Z$^2$, independently, are selected from —NR$^7$R$^8$. For example, in one embodiment, R$^7$, R$^8$, and R$^9$, independently, are selected from H, C$_1$-C$_6$ alkyl, C$_2$-C$_6$ alkenyl, and C$_2$-C$_6$ alkynyl. For example, in one embodiment, Z$^1$ and Z$^2$, independently, are selected from —NHR$^8$, wherein R$^8$ is as defined above. For example, R$^8$ may be selected from C$_{1-4}$ alkyl, such as methyl or ethyl. In one embodiment, Z$^1$ and Z$^2$ are independently selected from —NHCH$_3$ and —NH CH$_2$CH$_3$.

In one embodiment, the compound is a compound of formula (6) in which R$^1$, R$^2$, R$^3$, R$^4$, R$^5$, and R$^6$, independently, are selected from H; halo; —CN; —NO$_2$; —OH; —SH; —SO$_2$H; —SO$_2$NH$_2$; —NH$_2$; —CHO; and —COOH; Z$^1$ and Z$^2$, independently, are selected from —NR$^7$R$^8$; and R$^7$, R$^8$, and R$^9$, independently, are selected from H, C$_1$-C$_6$ alkyl, C$_2$-C$_6$ alkenyl, and C$_2$-C$_6$ alkynyl. In one embodiment, Z$^1$ and Z$^2$ are independently selected from —NHCH$_3$ and —NH CH$_2$CH$_3$.

In one embodiment, the compound is a compound of formula (6) in which R$^1$, R$^2$, R$^3$, R$^4$, R$^5$, and R$^6$, independently, are H; Z$^1$ and Z$^2$, independently, are selected from —NR$^7$R$^8$; and R$^7$, R$^8$, and R$^9$, independently, are selected from H, and C$_1$-C$_4$ alkyl. In one embodiment, Z$^1$ and Z$^2$ are independently selected from —NHCH$_3$ and —NH CH$_2$CH$_3$.

A second aspect of the invention provides a compound of Formula (7) or Formula (8):

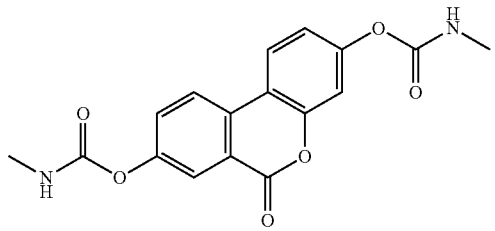

Formula (7)

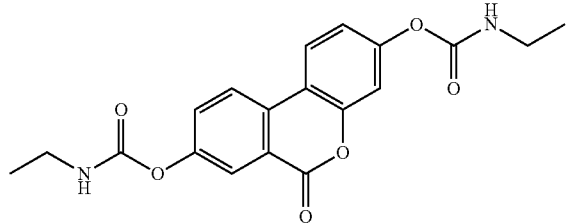

Formula (8)

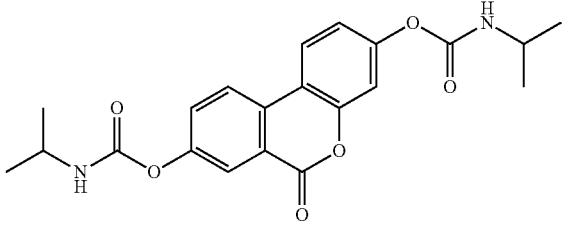

Formula (9)

In embodiment, the compound is a compound of Formula (7).

In embodiment, the compound is a compound of Formula (8).

In embodiment, the compound is a compound of Formula (9).

A third aspect of the invention provides pharmaceutically acceptable salt, solvate or prodrug of the compound of the first or second aspect of the invention.

For the purposes of this invention, a "salt" of a compound of the present invention includes one formed between a protic acid functionality (such as a carboxylic acid or alkyl sulphonic groups) of a compound of the present invention and a suitable cation. Examples of suitable salts include but are not limited to mesylate and tosylate. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, multi-salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

An sixth aspect of the invention provides the use of a compound of the first or second aspect, a pharmaceutically effective salt, solvate or prodrug of the third aspect, or a pharmaceutical composition according to the fourth aspect, in the manufacture of a medicament for the treatment or prevention of a disease, disorder or condition. Typically the treatment or prevention comprises the administration of the compound, salt, solvate, prodrug or pharmaceutical composition to a subject. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. Typically the administration is to a subject in need thereof. In one embodiment, the disease, disorder or condition is selected from the group consisting of mitochondrial diseases (including for example poor growth, loss of muscle coordination, muscle weakness, visual problems, hearing problems, heart disease, liver disease, kidney disease, gastrointestinal disorders, respiratory disorders, neurological problems, metabolic syndrome, cardiovascular disease, sarcopenia, muscle degenerative disease, liver diseases, nonalcoholic fatty liver disease (NAFLD), nonalcoholic steatohepatitis (NASH), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, or seventh aspect of the present invention, the disease, disorder or condition is selected from but not limited to: metabolic stress, cardiovascular disease, endothelial cell dysfunction, sarcopenia, muscle degenerative disease, Duchenne muscular dystrophy, alcoholic liver disease, nonalcoholic fatty liver disease, drug-induced liver injury, a 1-antitrypsin deficiency, ischemia/reperfusion injury, inflammation, aging of the skin, inflammatory bowel disease, Crohn's disease, obesity, metabolic syndrome, type II diabetes mellitus, hyperlipidemia, osteoarthritis, neurodegenerative disease, Alzheimer's disease, Huntington's disease, Parkinson's disease, amyotrophic lateral sclerosis, age-related macular degeneration, mitochondrial diseases (including for example poor growth, loss of muscle coordination, muscle weakness, visual problems, hearing problems, heart disease, liver disease, kidney disease, gastrointestinal disorders, respiratory disorders, neurological problems, autonomic dysfunction sometimes learning disabilities, and dementia as a result of mitochondrial disease), muscle diseases; sporadic inclusion body myositis (sIBM), cancer, cognitive disorder, stress, and mood disorder.

In one embodiment, the disease, disorder or condition is selected from but not limited to:

muscle degenerative disease, cardiovascular disease, sarcopenia, nonalcoholic fatty liver disease (NAFLD), ischemia/reperfusion injury, inflammatory bowel disease, Crohn's disease, type II diabetes mellitus, hyperlipidemia, neurodegenerative disease, Alzheimer's disease, Parkinson's disease, Huntington's disease, anxiety disorder, cancer.

In one embodiment, the disease, disorder or condition is a neurodegenerative disorder, such as Alzheimer's disease, Parkinson's disease, or ischemia.

Unless stated otherwise, in any aspect of the invention, the subject may be any human or other animal. Typically, the subject is a mammal, more typically a human or a domesticated mammal such as a cow, pig, lamb, goat, horse, cat, dog, etc. Most typically, the subject is a human.

Any of the medicaments employed in the present invention can be administered by oral, parental (including intravenous, subcutaneous, intramuscular, intradermal, intratracheal, intraperitoneal, intraarticular, intracranial and epidural), airway (aerosol), rectal, vaginal or topical (including transdermal, buccal, mucosal and sublingual) administration.

Typically, the mode of administration selected is that most appropriate to the disorder or disease to be treated or prevented.

For oral administration, the compounds, multi-salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, multi-salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For transdermal and other topical administration, the compounds, multi-salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, multi-salts, solvates or prodrugs of the present invention will, of course, vary with the disorder or disease to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

Compound Synthesis

Compounds of the invention are synthesised employing a route of synthesis shown below. The general route of synthesis is illustrated below by reference to the synthesis of a specific compound. However, this is merely illustrative of a more general synthesis that can be employed to synthesise all compounds of the invention.

Route of Synthesis:

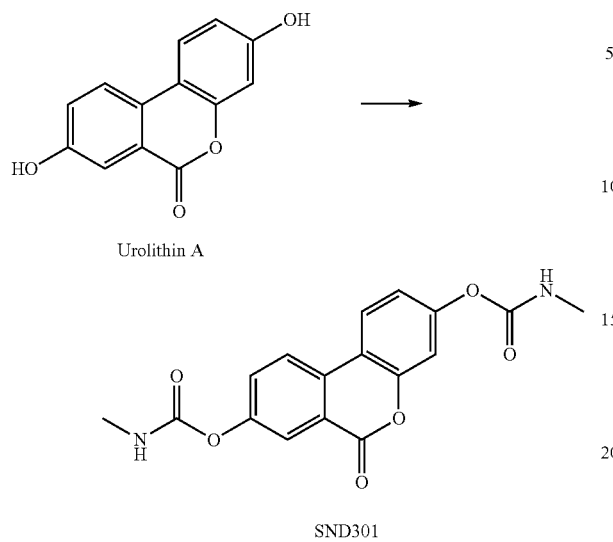

Urolithin A

SND301

EXAMPLES

Compound Synthesis

All solvents, reagents and compounds were purchased and used without further purification unless stated otherwise.

SND301 was prepared from Urolithin A using similar conditions to those reported in the literature; for example see J. Pandey et al, 2004, Bioorg. Med. Chem. 12 (2004) 2239-2249; for the analogous bis(dialkylamino) derivatives.

Stage 1

Using excess N-methyl carbamoyl chloride in pyridine, reaction occurred cleanly, but slowly, at 40° C. to produce target SND301.

Yields for the stage: 81% (Combined yield for two batches)

Experimental Procedures

A suspension of Urolithin A (200 mg, 0.88 mmol) in pyridine (8 mL) was treated with N-methyl carbamoyl chloride (0.49 g, 5.26 mmol) and stirred in a sealed vessel at 40° C. After 13 days, the reaction showed high conversion to product, as monitored by 1 cms. Solvent was removed in vacuo and the mixture was co-evaporated with EtOAc. The residue was slurried and sonicated (to break up chunks of material) in EtOH (30 mL) for 15 min. The procedure above was repeated starting with 50 mg of Urolithin A and similar ratios of pyridine and N-methyl carbonyl chloride. This second batch was added to the first batch and they were further purified together by trituration with 15 ml of anhydrous ethyl alcohol for 30 mins. Filtration removed the mono-acylated (minor) product.

The residue was dried in vacuo at 60° C. over KOH overnight to afford the product as a white solid, 305 mg, 81%.

$^1$H NMR (400 MHz, $d_6$-DMSO): δ 8.45 ppm (d, 1H), 8.35 (d, 1H), 7.90 (d, 1H), 7.87-7.81 (m, 1H), 7.81-7.75 (m, 1H), 7.71 (dd, 1H), 7.23 (d, 1H), 7.18 (dd, 1H), 2.85-2.80 & 2.74-2.69 (m, 6H). Rotamers confirmed by VT nmr.

The following nomenclature is employed throughout.

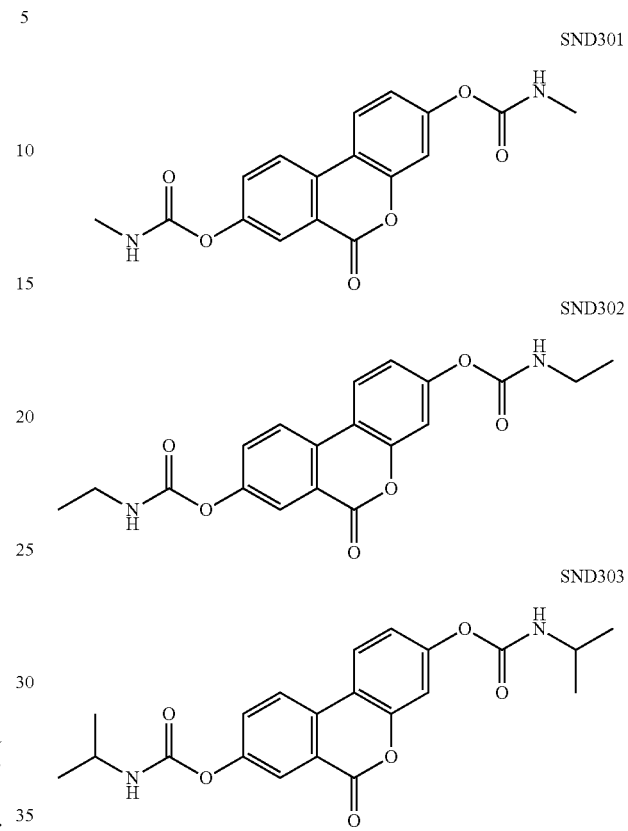

Examples

Biological Studies

Example 1: Cytotoxicity and Viability of Primary Human Hepatocytes Treated with SND301

Cytotoxicity potency of test compound SND301 was assayed in human hepatocytes from pooled donor lots at three concentrations; 1, 10 and 100 μM. Cytotoxicity was assayed from medium samples after 24 h exposure period with test compounds by measuring membrane integrity (LDH leakage), coupled to fluorescent signal. In parallel, cell viability was assayed by the means of ATP content, indicating the metabolically competent cell activity. ATP content was measured based on luciferase catalysed reaction generating stable bioluminescent signal. Cytotoxic positive control compound was used: chlorpromazine at 5-250 μM.

ATP content after incubation with SND301 at 1 to 100 μM was 72-103%. Thus, the results do not suggest loss in viability by these compounds in the hepatocytes.

Cytotoxicity (LDH) leakage after incubation with SND301 at 1 to 100 μM was 7-10% indicating no toxicity in the hepatocytes.

Experimental Procedure

Chemicals unless otherwise specified: Sigma Aldrich (Helsinki, Finland), the highest purity available. Water was in-house freshly prepared with a Direct-Q3 (Millipore Oy, Espoo, Finland) purification system and UP grade (ultra pure, 18.2 MΩ).

SND301 was dissolved in DMSO on the day of start of incubations (20 mM). Stocks were serially diluted in media before starting incubations and DMSO content was normalized.

Primary Hepatocyte Incubations

Cryopreserved human hepatocytes from pooled donor lot (Bioreclamation IVT) were seeded on collagen I coated 96-well plates (Corning Biocoat) at $0.55 \times 10^5$ cells per well in 120 µl InVitroGRO™ CP medium (BioIVT), including additives Torpedo Antibiotic mix (BioIVT). After cell attachment (4-6 hours post seeding) cell culture medium was replaced with fresh medium and incubated for 72 hours at 37° C. under 5% $CO_2$. Thereafter, hepatocytes were exposed to test or control compounds in 100 µl of InVitroGRO™ HI medium, including additives Torpedo Antibiotic mix at concentrations presented below. Cytotoxicity and cell viability were evaluated based on LDH release in medium and ATP content in the cells after 24 hours exposure phase.

A visual inspection of the cells was performed under light microscope before the cytotoxicity and cell viability assays.

Incubation Conditions

| Cell model/supplier | Cryopreserved pooled human hepatocytes in monolayer/(BIOIVT) |
|---|---|
| Conditions in the incubation after plating the cells: | |
| Incubation volume (exposure phase) | 100 µL |
| Number of cells/well | $5.5 \times 10^4$/96-well (after plating) |
| Test compound | 1, 10 and 100 µM in 3 replicates |
| Control compounds | Chlorpromazine (5, 50, and 250 µM) in 3 replicates, vehicle (DMSO), LDH max treatment prior to assay (9% w/vTriton-X) in 3 replicates |
| DMSO content in incubation | 0.5% |
| Duration of test compound exposure | 24 hr |
| Temperature/$CO_2$ | 37° C., 5% $CO_2$ |
| Determination of LDH | CytoTox-ONE ® Homogenous Membrane Integrity Assay (Promega) from the cell culture medium sample (50 µl) followed by fluorescence measurement; 560 nm excitation, 600 nm emission |
| Determination of ATP (only toxicity study) | CellTiter-Glo ® Luminescent Cell Viability Assay (Promega) from the cells, followed by luminescence measurement |
| Measurement | Synergy H1 hybrid multi-mode reader (BioTek Instruments); monochromator. |

After 24 h exposure half of the culture medium (50 µl) was transferred to black opaque-walled 96-well plate (Corning #3603) for LDH measurements and allowed to settle to room temperature. The LDH substrate solution (Promega) was added (50 µl) and the samples were further incubated 10 minutes at shaking, in room temperature. The generation of fluorescent product was stopped by adding a stop solution. Thereafter the samples were analysed with plate reader for fluorescence (LDH; $560_{ex}$, $590_{em}$).

Appropriate controls (chlorpromazine, total lysis, vehicle and medium) were simultaneously used as assay controls.

The remaining medium and cells were used for the assessment of metabolically competent cells (ATP) according to the manufacturer's (Promega) protocol. Briefly, luciferase substrate in buffer (Promega) was added (40 µl) and cells were vigorously shaken for 25 min to facilitate lysis. The samples were transferred to white opaque-walled 96-well plate (Corning #3610) after which measured with plate reader for luminescence.

Both LDH and ATP assays were measured 1-2 hours post treatment with assay components.

Example 2: Effect of Compounds on *C. elegans* Life Span

It has been recently showed that urolithin A (UA) as a first-in-class natural compound that induces mitophagy both in vitro and in vivo following oral consumption; see Ryu et al, 2016, "Urolithin A induces mitophagy and prolongs lifespan in *C. elegans* and increases muscle function in rodents", Nature Medicine, vol. 22, pages 879-888. In *C. elegans*, UA prevented the accumulation of dysfunctional mitochondria with age and extended lifespan.

Testing of SND301

In a first stage of this study, normal worms were treated with various concentrations of SND301 to test toxicity and food avoidance. Exposure to concentrations up to 50 µM of SND301 to N2 wild type strain of worms from embryo to first day of adulthood has been found to be well tolerated. The compound has not led to avoidance of bacterial food.

The survival assay was conducted in the presence of 50 µM SND301 with measurements of live, dead, and censored worms at time points every 2-3 days from the start of adulthood.

In this study, test SND301 significantly increased life span similar to Urolithin A, used at the same concentration of 50 µM. Thioflavin T was used in the assay as a positive control [Gamir-Morralla A et al, 2019, "Effects of Thioflavin T and GSK-3 Inhibition on Lifespan and Motility in a *Caenorhabditis elegans* Model of Tauopathy", J Alzheimers Dis Rep., 3(1): 47-57]. Vehicle 25% and 1% DMSO were used as controls and represent the vehicles in which compounds and bacteria or bacteria alone respectively were resuspended. The final DMSO concentration in the agar plates was 0.5% and 0.02% respectively. Results depicting the percentage of worms which died from aging at a certain point during the study are presented in Table 1A and show that increased death in the vehicle groups versus treated groups:

TABLE 1A

Death events-all death in the study; Censored-deaths from other causes outside aging; % complete-deaths attributed to aging from total worm population

| Condition | Strain | Treatment | Death events | Censored | % Complete |
|---|---|---|---|---|---|
| 1 | N2 | SND301 | 59 | 15 | 31.6 |
| 2 | N2 | Urolithin A | 47 | 14 | 25.7 |
| 3 | N2 | Thioflavin | 38 | 27 | 23.2 |
| 4 | N2 | Vehicle 25% DMSO | 69 | 20 | 40.6 |
| 5 | N2 | Vehicle 1% DMSO | 75 | 34 | 49.7 |

Table 1B depicts the median and maximum life span at the end of the study, as well as the statistical significance between treatments and control DMSO vehicle 1%. Worms treated with SND301 showed a significantly increased median lifespan. Whereas positive controls Urolithin A and Thioflavin T showed longer maximum lifespans due to a small number of surviving worms, SND301 showed the highest surviving fraction by a considerable margin until day 24.

TABLE 1B

| Treatment | Death events | Censored | Median life span (days) | Maximum life span (days) | Log-rank (Mantel-Cox) test [†] | Gehan-Breslow-Wilcoxon test [‡] |
|---|---|---|---|---|---|---|
| SND301 | 179 | 19 | 24 | 31 | <0.0001 **** | <0.0001 **** |
| Urolithin A | 178 | 16 | 21 | 35 | <0.0001 **** | 0.0004 *** |
| Thioflavin | 38 | 27 | 21 | 33 | <0.0001 **** | <0.0001 **** |
| Vehicle 25% DMSO | 168 | 22 | 21 | 26 | 0.0394 * | 0.0292 * |
| Vehicle 1% DMSO | 151 | 34 | 21 | 26 | NA | NA |

[†] Mantel-Cox test compares groups across the duration of the lifespan.

[‡] Gehan-Breslow-Wilcoxon test applies more weight to earlier deaths.

Numbers and asterisks represent P-value and significance, respectively.

Experimental Method:

Preparation of Compound Stocks 5 mM DMSO stock solutions for each compound were prepared in high-grade DMSO. Stocks were protected from light and stored in glass vials at 21° C. in a temperature-controlled room (to avoid freeze/thaw of DMSO). A fresh stock was prepared at the start of each experiment and stored for <1 week.

To test food avoidance worms were placed on agar plates containing a grid of alternating control and compound-containing food spots. The number of worms on each food spot was recorded every two hours. No significant differences in preference or avoidance were observed with either compound or vehicles.

Life Span Assay

The lifespan assay was designed and performed according to published and validated methods with modifications for chemical treatment [Amrit F R G et al, 2014, "The C. elegans lifespan assay toolkit", METHODS 68, 465-475; Leukanic, et. Al, "Manual Lifespan Assay Standard Operating Procedure", Caenorhabditis Intervention Testing Program, https://figshare.com/articles/7_CITP_SOP_Manual_Lifespan_Assay/9738197/1]. Plates were seeded with compound dissolved in 25% DMSO and bacteria. The DMSO diffused through the agar to reach a final concentration of 0.5%. Synchronized day 1 adult worms were transferred to seeded plates containing compound and allowed to lay eggs for 2 hours (Day 0, "hatchoff"). The young adults were then removed, and the eggs were incubated at 20° C. until they had reached the young adult stage (day 3). 200 young adult worms per treatment were transferred to 8 fresh seeded 35 mm dishes with compound and 50 µM 5-Fluorodeoxyuridine to suppress progeny. Worms were scored three times a week as "alive," "dead," or "censored." Worms that failed to move with three gentle prods (tail, midbody, head) were scored as "dead" and removed. Worms that were missing, stuck to the dish, burrowed, injured, or exploded were scored as censored and removed from the plate. To maintain chemical exposure at the experimental concentrations, worms were transferred every other scoring day to new seeded plates with compound.

Testing of SND302 & SND303

An additional life span assay using an adapted standard protocol employed and published by the C. elegans Intervention Testing Program, or CITP was employed to assess the activity of SND302 and SND303. A positive and a negative control were included in the assay. In a preliminary experiment the optimal conditions for the life span analysis was determined and the stress level induced by the compounds as well as toxicity were measured.

The working EC 50 for each compound was determined by measuring physiological stress in response to varying concentrations using a fluorescent C. elegans stress biosensor strains. Transgenic biosensor worms express red fluorescent protein (RFP) in response to stress and constitutively express green fluorescent protein (GFP). Two of the biosensors utilize reporters in the same class of heat shock response genes shown previously to be unaffected by Urolithin A [Ryu, D. et al. Urolithin A induces mitophagy and prolongs lifespan in C. elegans and increases muscle function in rodents. Nature Medicine 22, 879-888 (2016)]. Day 1 adult biosensor worms were treated with a range of 12.5 µM-200 µM of each compound. Fluorescent images were captured after 24 hours of treatment and stress response was quantified by normalizing the RFP signal to the GFP signal. Compounds SND3 derivatives were soluble up to 50 µM in 25% DMSO. Compounds were delivered by covering food bacteria with DMSO stock solution then chasing with sterile water to distribute the drug across the entire plate. No effect was detected on three biosensor strains treated with the compounds. Growth, viability, and toxicity assays indicated a maximum non-toxic dosage of 50 µM for all compounds. Based on this data, a concentration of 25 µM for all compounds for both lifespan assay and transcriptome analysis was chosen.

For the life span assay over 300 worms per conditions were used and the study was conducted by InVivoBiosystems (USA) using an Automated Lifespan Machine (ALM) with proprietary modifications to improve temperature stability and image acquisition.

Of the SND compounds tested, SND303 had the greatest positive effect on lifespan. SND303 showed a clear and statistically significant lifespan extension compared to controls and to Urolithin A. Results are depicted in Table 2 and the statistical analysis in Table 3. Among the treatment groups, worms treated with SND303 overall lived significantly longer than those treated with vehicle and had both the highest median and maximum lifespan of all groups (Table 2). Worms treated with SND302 did not show a significant difference from the control. Likewise, Urolithin A also did not produce a significant change in lifespan. Resveratrol at 50 µM was used as a positive control in the assay.

TABLE 2

Lifespan assay summary. Median lifespan is equal to the time at which 50% of the subjects have died. Mean lifespan is calculated from the area under the survival curve. Maximum shown here is the average lifespan of the ten longest-lived worms in each group.
C.L: Confidence Interval.

|  | Vehicle (0.5% DMSO) | SND302 (25 µM) | SND303 (25 µM) | Uro A (50 µM) | Resveratrol (50 µM) |
|---|---|---|---|---|---|
| Number of Worms | 302 | 271 | 350 | 236 | 372 |
| Median lifespan (days) | 27-5 | 28.2 | 29.0 | 27.8 | 28.2 |
| Median 95% C.I. | 26.9-27.9 | 27.3-28.8 | 28.4-29.6 | 26.9-28.5 | 27.5-28.8 |
| Mean lifespan (days) | 27.0 | 27.0 | 27.6 | 27.0 | 27-3 |
| Mean 95% C.I. | 26.4-27.5 | 26.4-27.7 | 27.0-28.2 | 26.4-27.6 | 26.9-27.9 |
| Maximum lifespan (days) | 35-9 | 36.1 | 37-2 | 34-4 | 36.6 |

TABLE 3

Pairwise statistical analysis of the lifespan assay. The Mantel-Cox Log-rank test. Numbers and asterisks represent P-value and significance, respectively.

| Curve comparison | Test statistic ($\chi 2$) | Log-rank test P-value |
|---|---|---|
| SND302 vs Vehicle. | 2.24 | 0.13 |
| SND303 vs Vehicle. | 12.28 | <0.005** |
| SND303 vs Urolithin A | 7.96 | <0.005** |
| Urolithin A vs Vehicle | 0.02 | 0.89 |
| Resveratrol vs Vehicle | 1.04 | 0.31 |

The age of the worms associated with mortality is presented in Table 4 and shows the increased survival induced by SND303.

TABLE 4

| | Age in days at % mortality. | | | | |
|---|---|---|---|---|---|
| Treatment | 25% | 50% | 75% | 90% | 100% |
| Vehicle | 24 | 27-5 | 30.3 | 32.4 | 37.8 |
| SND302 | 24.2 | 28.2 | 31.0 | 33.0 | 37.9 |
| SND303 | 25 | 29.0 | 31.8 | 33.9 | 39.9 |
| Uro A | 23.8 | 27.8 | 30.2 | 32.3 | 37.7 |
| Resveratrol | 24.6 | 28.2 | 30.5 | 32.7 | 37.8 |

Experimental Method:
Worm Maintenance and Media

To prevent chemical modification or metabolism of the test article by the food bacteria, worms were fed on a lawn of UV-killed bacteria (UV-i bacteria). An overnight culture of E. coli strain WP-2 was pelleted, washed, filtered, and irradiated. A suspension of UV-i bacteria was spotted on NGM agar containing Streptomycin to inhibit growth of contaminating bacteria. The quantity and distribution of food bacteria was calibrated to ensure adequate access to food for the duration of assay while maintaining visibility of the worms.
Test Article Dosing and Delivery Test article was delivered to worms by a method compatible with and previously validated on the Automated Lifespan Machine and used by the CIT [Lucanic, et. al. Impact of genetic background and experimental reproducibility on identifying chemical compounds with robust longevity effects. Nature Communications 8 (2017)]. A 200× stock solution was freshly prepared in DMSO immediately before application. 40 µl of DMSO stock (0.5% plate volume) was applied to the plate to coat the food bacteria and then chased immediately with 160 µl water to uniformly distribute a fine precipitate across the surface of the plate. This functioned to provide reservoirs of compound in food, agar, and agar surface.
Viability/Developmental Delay Assay For each concentration of compound, 20 day 1 adult worms were transferred to a dish containing compound and allowed to lay eggs for 2 hours (day 0, "hatchoff"). Exactly 50 eggs were transferred to each of 3 replicate plates containing food/compound mixture. At day 1, the number of larvae and unhatched eggs were scored. For days 2 and 3 the number of L2/L3 larvae, L4 larvae, and adult worms were scored. Plates were imaged each day, and the size of the worms extracted using WormLab software (MBF Bioscience).
Automated Lifespan Machine (ALM)

The ALM used by InVivoBiosystems is based on the Caenorhabditis elegans lifespan machine published by Stroustrup, N. et al. The Caenorhabditis elegans Lifespan Machine. N at Methods 10, 665-670 (2013), with proprietary modifications to improve temperature stability and image acquisition. The scanner unit consists of a modified EPSON V850 and images are processed and analyzed using the ALM software 7. The machine time-of-death calls are trained and validated using the "storyboarding" feature of the ALM software.
Lifespan Assay The lifespan assay was designed and performed according to published and validated methods, Amrit, F. R. G., Ratnappan, R., Keith, S. A. & Ghazi, A. The C. elegans lifespan assay toolkit. Methods 68, 465-475 (2014); Lucanic, et. al. Manual Lifespan Assay Standard Operating Procedure. Caenorhabditis Intervention Testing Program https://figshare-.com/articles/7_CITP_SOP_Manual_Lifespan_Assay/9738197/1. using a modified version of the Automated Lifespan Machine. Worms were age synchronized by bleaching and eggs were plated directly onto NGM agar seeded with UV-I bacteria (Day 1, hatch). On Day 3, when the worms had reached the late L4 stage, they were transferred to dishes containing 100 µM 5-Fluorodeoxyuridine (FUdR) to suppress progeny. On day 5, the worms were washed off the dishes and 30-50 worms were plated on each scanner dish. Plates were immobilized inverted on the bed of an Automated Lifespan Machine which scanned two images per hour of the plates continuously for the next 40 days.
Survival Analysis Time of death calls exported from the ALM software were analyzed and plotted using the Lifelines software package developed by Davidson-Pilon, (2019). lifelines: survival analysis in Python. Journal of Open Source Software, 4(40), 1317.

Example 3: Effect of the Compounds on Gene Expression—Whole Transcriptome Analysis To determine the mode of action for SND302 and SND303 the gene transcription in young and aged adults was analyzed by RNA-Seq (whole transcription analysis). For each condition, >300 worms were treated in parallel with the lifespan assay and maintained under identical conditions.

Differential gene expression was performed with EdgeR using false likelihood ratio tests based on fitting linear models. The likelihood ratios were used to determine the p-values which were subsequently corrected for using the BH false discovery rate (fdr) method. Eventually, differential expressed genes were defined as genes with fdr-corrected p-value of 0.05 or lower, as well as a change in expression of at least 2-fold in a given between-group comparison. Compounds SND302 and SND303 were compared against Urolithin and Vehicle control. Urolithin A (Uro-A) and the vehicle control showed similar results to each other (no differentially-expressed genes) and are referred as controls. SND302 showed some signs of toxicity and stress response induction during the early exposure period. SND303 had the most interesting response, with few genes significantly changing, but the patterns of gene expression were different from SND302. SND303 did not induce a large number of immune response genes, but rather genes which regulate oxidative/reductive properties in the cell/organism, as well as a significant upregulation of a gene linked to well-known longevity-linked genes in the Day 10 condition (at the Day 10 timepoint). In general the transcriptomic data corroborates a differential effect for SND303 when compared to SND302 (FIGS. 1-4).

Figure 2:
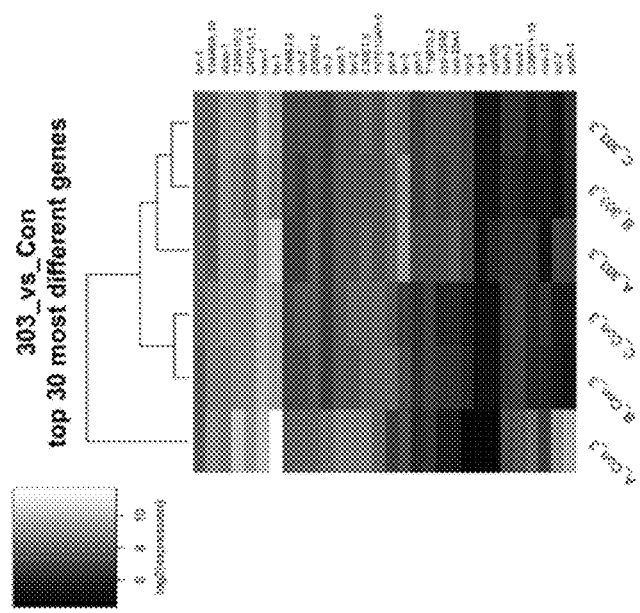
FIG. 2 shows heat maps and table depicting top 30 differentially-expressed genes in SND303-treated vs. control (Uro-A or Vehicle) animals at day 3 of adulthood. Black indicates downregulated genes and white upregulated genes.
Figure 2:
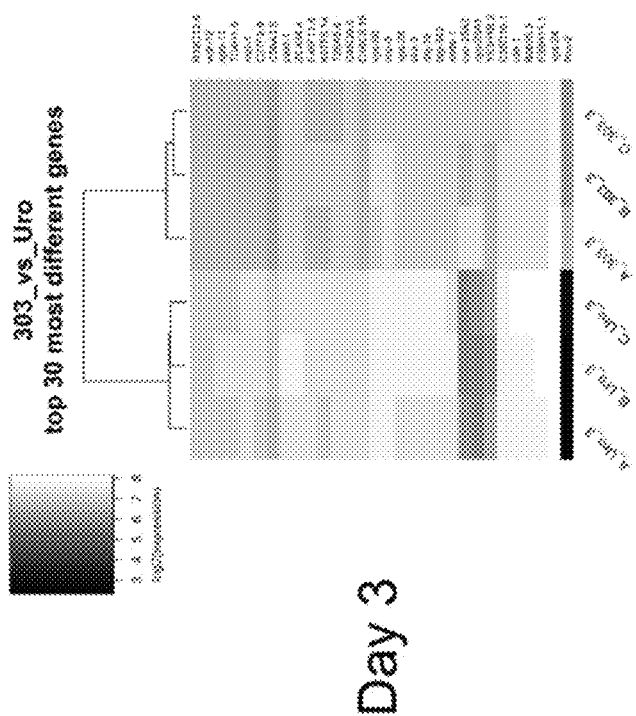

Day 3 comparisons are presented in FIGS. 1 and 2 (SND302 and SND303 respectively). SND302-treated worms had 7-8 significant differentially-expressed genes compared to the Controls (Vehicle and Urolithin A). These are: irg-4, irg-5, T01D3.6, fmo-2, gst-4, asp-1, cyp25A1, clec-67, B0035.13 and C49C8. All of these genes were upregulated. There were no genes with significantly decreased expression relative to controls. GO terms for immune response, peptidase activity, xenobiotic response, and oxidoreductase activity were enriched, and there were no GO terms that were under-represented.

SND303-treated worms had 2-3 significant differentially-expressed genes compared with the controls. These are: cyp25A1, fmo-2; irg-5 and far-3. The enriched GO terms were focused around oxidative-reductive processes, metal/heme binding, and cofactor binding. No GO terms were under-represented.

FIG. 1 shows heat maps and table representing top 30 differentially-expressed genes in SND302-treated vs. control (Uro-A or Vehicle) animals at day 3 of adulthood.

FIG. 2 shows heat maps and table representing top 30 differentially-expressed genes in SND303-treated vs. control (Uro-A or Vehicle) animals at day 3 of adulthood.

Figure 3:
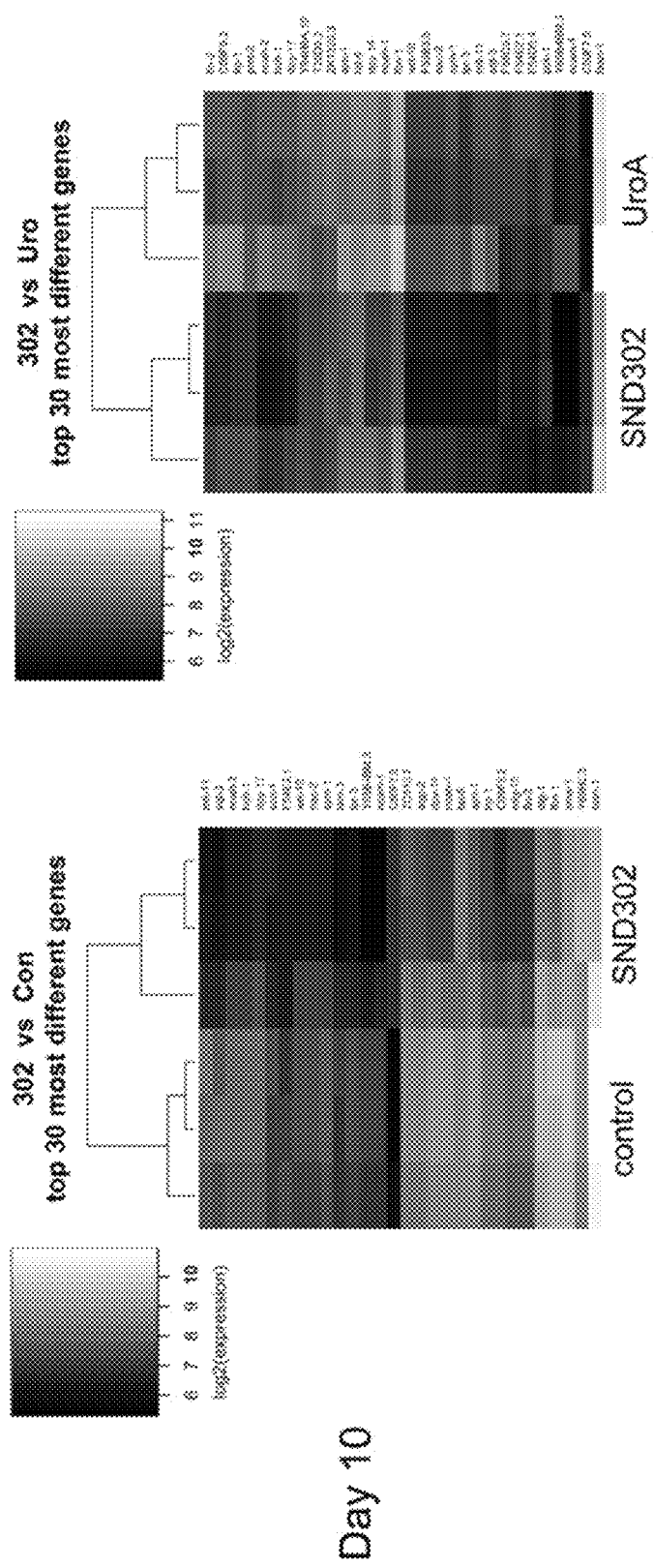
FIG. 3 shows heat maps and table representing top 30 differentially-expressed genes in SND302-treated vs. control (Uro-A or Vehicle) animals at day 10 of adulthood. Black indicates downregulated genes and white upregulated genes.
Figure 4:
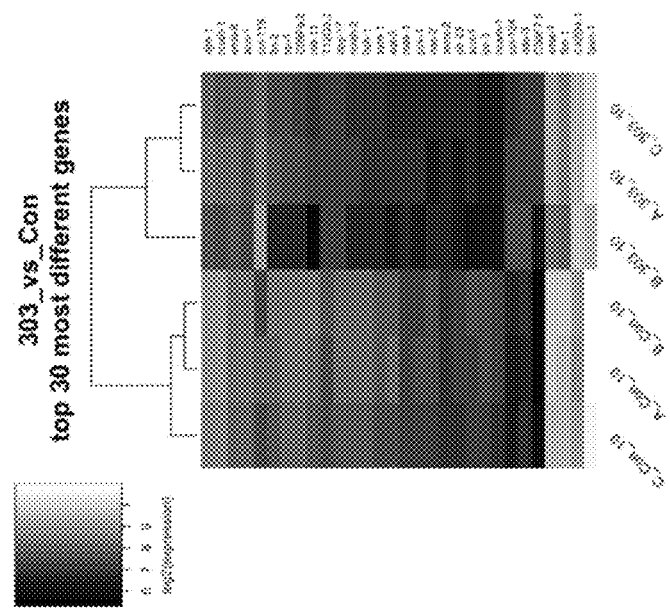
FIG. 4 shows heat maps and table representing top 30 differentially-expressed genes in SND303-treated vs. control (Uro-A or Vehicle) animals at day 10 of adulthood. Black indicates downregulated genes and white upregulated genes.
Figure 4:
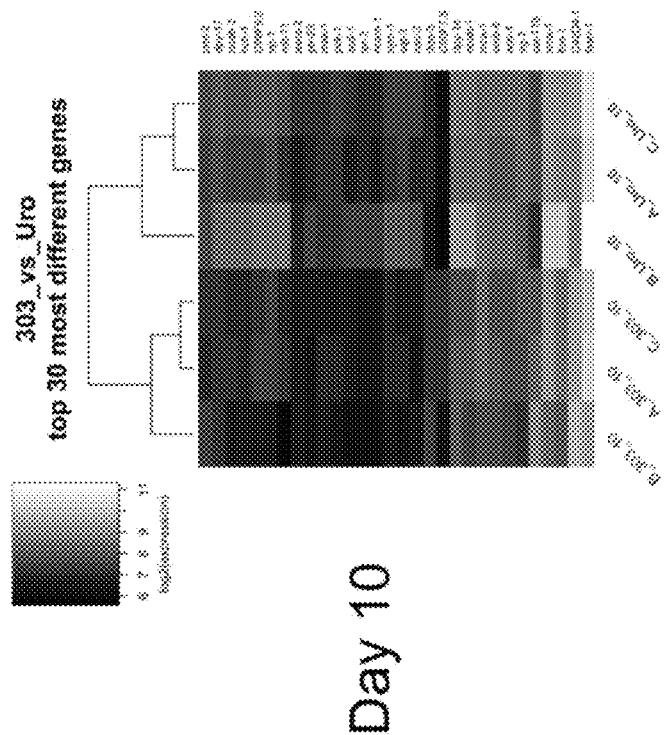

Day 10 comparisons are presented in FIGS. 3 and 4 (SND302 and SND303 respectively) SND302 treated worms had 12-14 significant differentially-expressed genes compared to the controls. These are: sqt-3, hch-1, noah-2, dpy-17, mlt-11, noah-1, ncam-1, fbn-1, dpy-14, C50F7.5, C09F9.2, Y65B4BM.3, fasn-1. All of these genes were down-regulated, except for one gene with significantly increased expression relative to the vehicle control, but not relative to UroA. The gene C50F7.5 was significantly upregulated in SND 302, and SND303, and it has been shown to be linked with known longevity genes daf-16, daf-2, and glp-1. No GO terms were significantly enriched. GO terms for cuticle formation, molting, and membrane transport were under-represented.

SND303 treated worms had 3 significant differentially-expressed genes compared with the UroA control (sqt-3, hch-1 and fbn-1, all decreased expression) and 7 most significant differentially-expressed genes compared to vehicle, with 6 down-regulated (sqt-3, hch-1 and fbn-1, mlt-11, C09F9.2 and noah-2) and the one up-regulated being the previously mentioned C50F7.5 gene. SND303 was the only compound that showed a somewhat stable GO enrichment profile from Day 3 to Day 10. Day 10 worms continued to show an upregulation of pathways related to oxidative-reductive activity in the cell and additionally showed an enrichment of amino acid metabolism and catabolism pathways. Even more interestingly, there was a significant under-representation of genes for GO terms related to "positive regulation of growth", implying that SND303 may be negatively regulating growth signalling pathways as a mechanism of increasing longevity.

FIG. 3 shows heat maps and table representing top 30 differentially-expressed genes in SND302-treated vs. control (Uro-A or Vehicle) animals at day 10 of adulthood.

FIG. 4 shows heat maps and table representing top 30 differentially-expressed genes in SND303-treated vs. control (Uro-A or Vehicle) animals at day 10 of adulthood.

Experimental Method:
Whole Transcriptome Analysis

Worms for RNA-Seq were split from the same synchronized pool of worms for the lifespan with each of the three replicates being maintained and treated in parallel. More than 150 worms per replicate were harvested, cleaned by filtration, and frozen at −80° in Trizol. To extract RNA, samples were thawed, vigorously vortexed, and processed using the Direct-zol RNA Miniprep Kit (Zymo Research). All samples exceeded our threshold for RNA quantity and quality. RNA samples were submitted to Novogene Co. Ltd and subjected to more stringent QC, being tested on a Qubit for concentration and run on an agarose gel and on the Agilent 210 assess RNA quality and integrity. All samples had an RNA Integrity Number (RIN) of 8.8 or higher (range is 0-10, with 10 being "perfect"). The total RNA was then enriched for poly-mRNA using oligo(dT) paramagnetic beads. DNA libraries were then constructed from this input mRNA using the NEBNext Ultra™ II RNA Library Prep Kit.

These libraries were then further tested by the Qubit for concentration and the Agilent 2100 for library size distribution and quality. In order to properly pool the libraries and load them onto sequencing lanes to ensure the correct number of reads per sample, an even more precise quantification of the library was done via qPCR, and the samples were loaded onto the NovaSeq 6000 platform for a paired-end sequencing run of 150 bp for each end (PE150). The loading concentrations were designed to obtain at least 6.0 Gb (which is the number of billion bases of raw data, determined by the number of reads multiplied by the length of each read). A mean of 7.4 Gb (median 7.3 Gb) raw sequencing data was obtained across all samples, with a minimum of 6.3 Gb and a maximum of 8.5 Gb raw data. Sequencing run data quality control was performed both by Novogene and by an in-house analysis. The raw data set was analyzed for parameters such as the distribution of base quality along the length of the sequencing read, the distribution of error rate along the length of the sequencing read. Reads containing adapter sequences, with N>10% (where N means "base cannot be determined") and with a low quality (Qscore<=5) for 50% or more of its total bases were removed.

Example 4: Pathway Analysis and Mechanism of Action

To determine which among recognized aging-related pathways were most likely modulated by treatment with the SND303 compound, and to estimate their relative contributions, two approaches were undertaken. In one approach, the genes differentially expressed after treatment were mapped to pathways in the KEGG database, a curated knowledge-base of biological pathways. This placed the transcriptomic data within the context of well-characterized biological pathways, particularly several related to longevity.

In the second approach, the transcriptomic profile of worms treated with SND303 compound was compared with published transcriptomes in which specific aging-related pathways have been manipulated. In contrast with the first approach, this blindly scores how the data fits with published transcriptomic signatures of aging.

Figure 5:
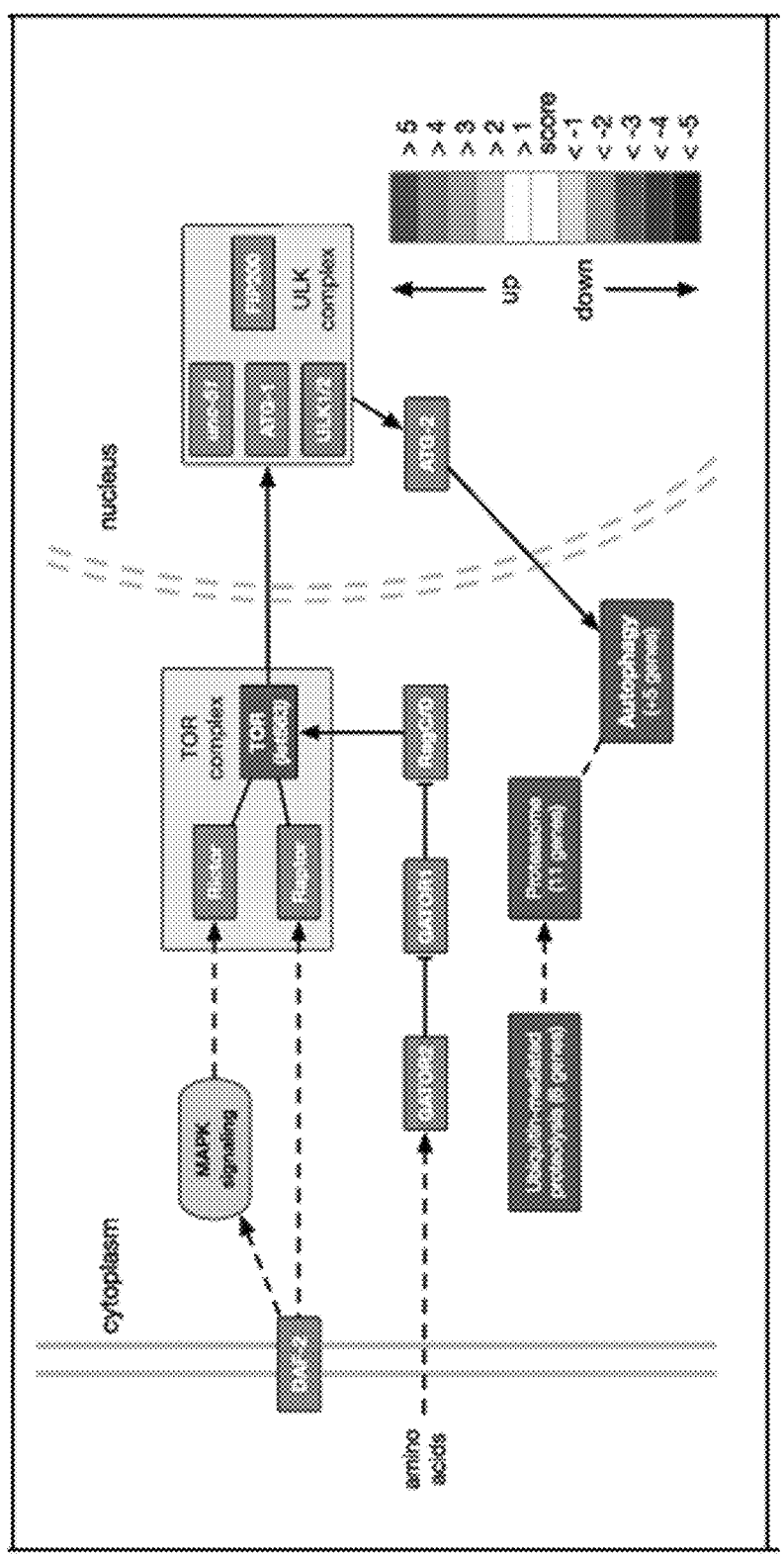
FIG. 5 shows the connectivity of aging-related pathways affected by SND303.

Despite producing a relatively small number of differentially-expressed genes, the response to SND303 showed disproportionately greater enrichment of differentially-expressed genes among KEGG pathways (Table 5) relative to other controls. Several of these genes matched to the canonical longevity pathways as curated in KEGG (FIG. 5). At Day 3, several genes involved in xenobiotic response were, unexpectedly, downregulated. At Day 10, however, many more pathways were represented among differentially-expressed genes and each individual pathway was more richly populated with differentially-expressed genes. The most prominent increase was in the expression of genes involved in Oxidative Phosphorylation, possibly indicating maintenance of mitochondrial function. In addition, several components of the canonical Longevity Regulating Pathway are represented. With closer examination of these the differential expression of the gene encoding Target of Rapamycin (TOR) is notable. When the TOR pathways itself was expanded, several more differentially-expressed genes were represented that were not explicitly indicated in the Longevity Regulating Pathway. Applying this process with the other pathways and modules linked to the Longevity Regulating Pathway, a coherent hypothetical pathway of action emerges. Interestingly, all of the differentially-expressed genes mapped to this group of pathways were downregulated relative to control. Although few of these differentially-expressed genes individually have highly significant changes in expression, collectively they suggest a hypothesis that modulation of the TOR pathway contributes to the observed lifespan effects of SND303 treatment.

TABLE 5

Top 12 KEGG pathways enriched with differentially-expressed genes from SND303 treatment.

| PATHWAY | Genes |
| --- | --- |
| Day 3 | |
| cel00980 Metabolism of xenobiotics by cytochrome P450 | gst-4; Glutathione S-transferase 4 sodh-1; Alcohol dehydrogenase 1 gst-5; Probable glutathione S-transferase 5 |
| cel04212 Longevity regulating pathway | gst-4; Glutathione S-transferase 4 gst-5; Probable glutathione S-transferase 5 ctl-2; Peroxisomal catalase 1 |
| Day 10 | |
| cel00190 Oxidative phosphorylation | 15 genes |
| cel03050 Proteasome | 11 genes |
| cel03040 Spliceosome | 10 genes |
| cel04140 Autophagy | let-363; Target of rapamycin homolog daf-15; Raptor_N domain-containing protein pek-1; Eukaryotic translation initiation factor 2-alpha kinase pek-1 atg-2; Autophagy-related protein 2 cpl-1; Cathepsin L-like |

TABLE 5-continued

Top 12 KEGG pathways enriched with differentially-expressed genes from SND303 treatment.

| PATHWAY | Genes |
| --- | --- |
| | epg-7; ATG11 domain-containing protein ragc-1; RAs-related GTP binding protein C homolog unc-51; Serine/threonine-protein kinase unc-51 |
| cel04150 mTOR signaling pathway | let-363; Target of rapamycin homolog daf-15; Raptor_N domain-containing protein rict-1; RICTOR_V domain-containing protein T08A11.1; DEP domain-containing protein ragc-1; RAs-related GTP binding protein C homolog Y32H12A.8; WD_Repeats domain-containing protein daf-2; Insulin-like receptor subunit beta unc-51; Serine/threonine-protein kinase unc-51 |
| cel04212 Longevity regulating pathway-worm | let-363; Target of rapamycin homolog sod-2; Superoxide dismutase [Mn] 1, mitochondrial gst-7; Probable glutathione S-transferase 7 fat-6; Delta(9)-fatty-acid desaturase fat-6 daf-2; insulin-like receptor subunit beta unc-51; Serine/threonine-protein kinase unc-51 |
| cel04361 Axon regeneration | 7 genes |
| cel04010 MARK signaling pathway | mtk-1; Protein kinase domain-containing protein fln-2; FiLamiN (actin binding protein) homolog nsy-1; Mitogen-activated protein kinase kinase kinase nsy-1 mnk-1; MAP kinase-interacting serine/threonine-protein kinase mnk-1 pxf-1; Rap guanine nucleotide exchange factor ced-2; Cell death abnormality protein 2 daf-2; Insulin-like receptor subunit beta |
| cel04141 Protein processing in endoplasmic reticulum | pdi-2; Protein disulfide-isomerase 2 cup-2; Derlin-1 skr-2; SKp1 Related (ubiquitin ligase complex component) pek-1; Eukaryotic translation initiation factor 2-alpha kinase pek-1 uggt-1; UDP-Glucose Glycoprotein glucosylTransferase nsy-1; Mitogen-activated protein kinase kinase kinase nsy-1 rbx-1; RING-box protein 1 Protein transport protein Sec61 subunit gamma |
| cel04120 Ubiquitin mediated proteolysis | 6 genes |

FIG. 5 shows the connectivity of aging-related pathways affected by SND303. Coloured score increments indicate degree of up-(red) or down-(blue) regulation weighted by the log of the P-value. Solid lines indicate direct pathway connections and dashed lines indicate indirect or multi-step connections. Where lists of differentially-expressed genes have been condensed into a module, the number of genes is indicated.

Pathway Transcriptional Profile Score Analysis

Frequently cited and relevant studies analyzing the transcriptomic signatures of aging-related pathways in *C. elegans* were selected for this analysis. From the published datasets, significantly affected genes as well as their direction of change in expression were aggregated. To generate a transcriptional profile score, the log fold change for each key gene in each pair of comparison (e.g. SND303 vs. negative control) is multiplied by a direction-specific factor and assigned a positive or negative value based on whether the change is in the same direction as reported in the literature. All the gene scores for a given pathway are summed up to produce one aggregated score per pathway for each pair of comparison. In this quantification, a positive score indicates that gene expression changes of key genes in a pathway is consistent with life-extension effects observed in literature.

Figure 6:
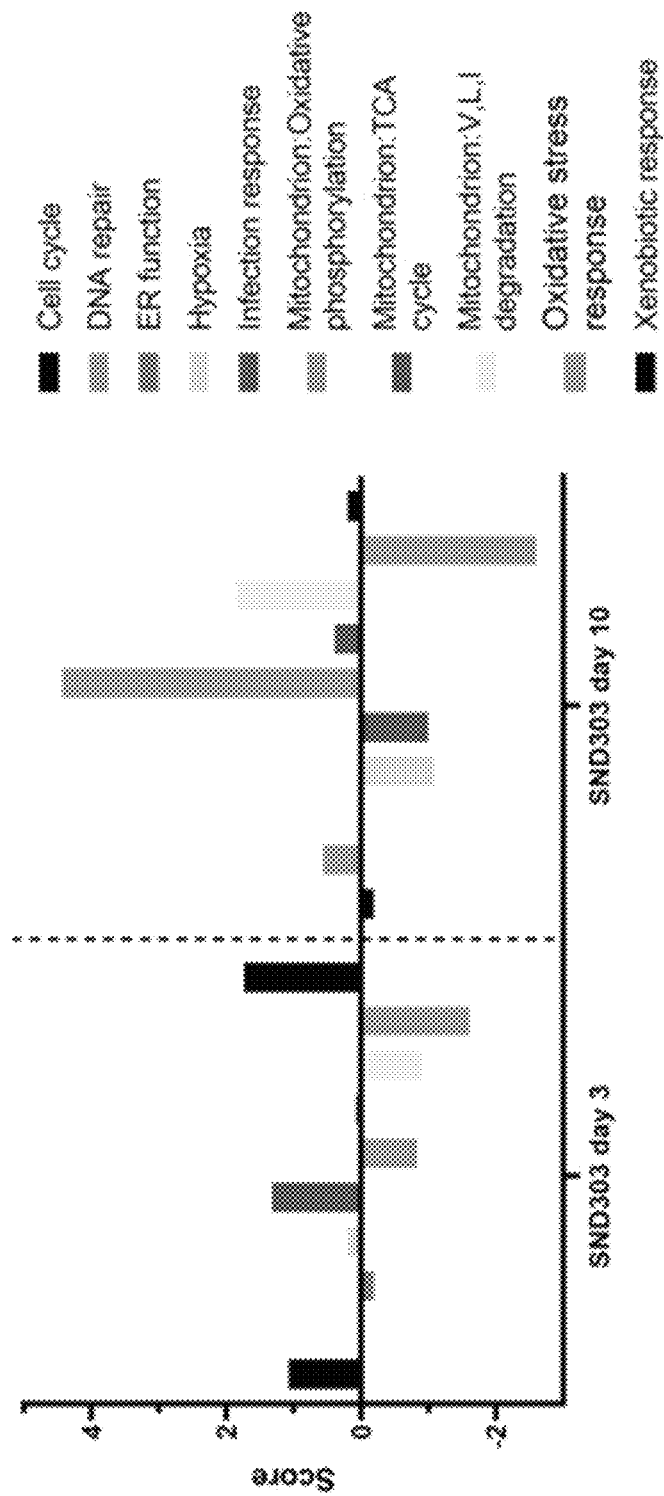
FIG. 6 shows a summary of pathway score for SND303 compared against negative control, at 3 days and 10 days of age.

The transcriptional profile score plot in FIG. 6 does not indicate activation or repression of a specific pathway, but whether the observed changes in expression fit—positively or negatively—with the expected direction of gene expression change extracted from published data. For example, at Day 10 SND303 shows a strong negative score in the Oxidative stress response, indicating their overall effect contrasts the effect expected under conditions that would normally activate this pathway.

SND303 showed little deviation from the control at Day 3, but then showed the greatest overall profile contrast with control at Day 10. The most prominent change was in the signature of increased mitochondrial function. This is consistent with the increase in expression of genes involved with oxidative phosphorylation observed in the KEGG analysis in the lifespan assay.

FIG. 6 shows a summary of pathway score for SND303 compared against negative control, at 3 days and 10 days of age.

The invention claimed is:

1. A compound of formula (1):

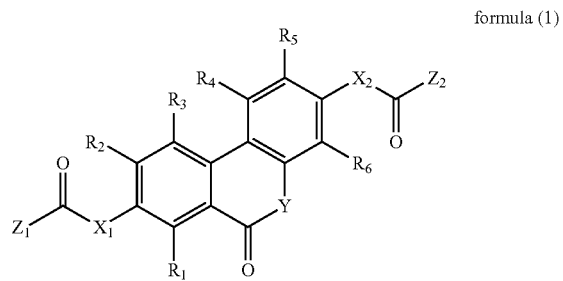

formula (1)

or a pharmaceutically acceptable salt or solvate thereof, wherein:

Y, $X_1$ and $X_2$ are —O—;

$R_1$, $R_2$, $R_3$, $R_4$, $R_5$, and $R_6$ are H; and $Z_1$ and $Z_2$, independently, are $NHR^8$; wherein $R^8$ is selected from methyl and propyl.

2. The compound according to claim 1, wherein $Z_1$ and $Z_2$ are —NHCH(CH$_3$)$_2$ or a pharmaceutically acceptable salt or solvate thereof.

3. The compound according to claim 1, wherein $Z_1$ and $Z_2$ are —NHCH$_3$ or a pharmaceutically acceptable salt or solvate thereof.

4. The compound according to claim 1, wherein the compound is a compound of Formula 7

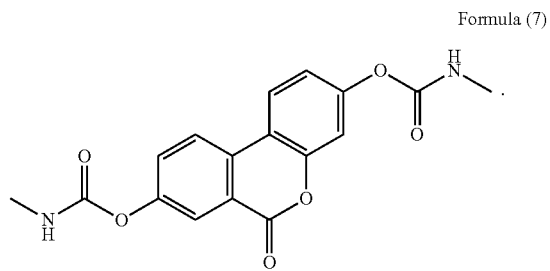

Formula (7)

5. The compound according to claim 1, wherein the compound is a compound of Formula (9):

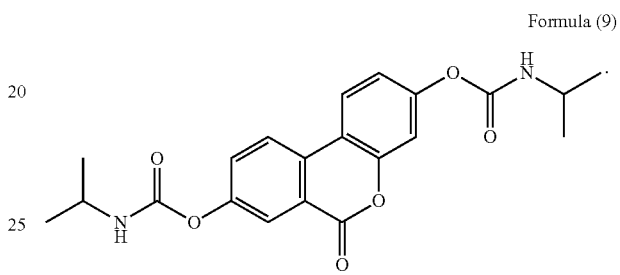

Formula (9)

6. A pharmaceutical composition comprising the compound according to claim 1, or a pharmaceutically acceptable salt or solvate thereof, and a pharmaceutically acceptable excipient.

7. A method of treatment of a disease, disorder or condition selected from metabolic stress, cardiovascular disease, endothelial cell dysfunction, sarcopenia, muscle degenerative disease, Duchenne muscular dystrophy, alcoholic liver disease, non-alcoholic fatty liver disease (NAFLD), drug-induced liver injury, a 1-antitrypsin deficiency, ischemia/reperfusion injury, inflammation, aging of the skin, inflammatory bowel disease, Crohn's disease, obesity, metabolic syndrome, type II diabetes mellitus, hyperlipidaemia, osteoarthritis, neurodegenerative disease, Alzheimer's disease, Huntington's disease, Parkinson's disease, amyotrophic lateral sclerosis, age-related macular degeneration, mitochondrial diseases, loss of muscle coordination, muscle weakness, visual problems, hearing problems, heart disease, liver disease, kidney disease, gastrointestinal disorders, respiratory disorders, neurological problems, autonomic dysfunction learning disabilities, dementia as a result of mitochondrial disease, muscle diseases, sporadic inclusion body myositis (sIBM), cancer, cognitive disorder, stress, anxiety disorder, and mood disorder, in a subject in need thereof, the method comprising the step of administering an effective amount of the compound according to claim 1, alone or in combination with a pharmaceutically acceptable excipient, to thereby treat the disease, disorder or condition.

* * * * *